(12) United States Patent
Boesze-Battaglia

(10) Patent No.: US 11,273,227 B2
(45) Date of Patent: Mar. 15, 2022

(54) COMPOSITIONS AND METHODS USEFUL IN TREATING STARGARDT'S DISEASE AND OTHER OCULAR DISORDERS

(71) Applicant: The Trustees of the University of Pennsylvania, Philadelphia, PA (US)

(72) Inventor: Kathleen Boesze-Battaglia, Haddon Heights, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 675 days.

(21) Appl. No.: 15/766,973

(22) PCT Filed: Oct. 7, 2016

(86) PCT No.: PCT/US2016/055963
§ 371 (c)(1),
(2) Date: Apr. 9, 2018

(87) PCT Pub. No.: WO2017/062750
PCT Pub. Date: Apr. 13, 2017

(65) Prior Publication Data
US 2019/0060487 A1 Feb. 28, 2019

Related U.S. Application Data

(60) Provisional application No. 62/239,480, filed on Oct. 9, 2015.

(51) Int. Cl.
| | |
|---|---|
| *A61K 48/00* | (2006.01) |
| *C07K 14/47* | (2006.01) |
| *C12N 15/86* | (2006.01) |
| *A61K 9/00* | (2006.01) |
| *A61K 38/17* | (2006.01) |
| *A61K 38/00* | (2006.01) |
| *A61K 39/00* | (2006.01) |

(52) U.S. Cl.
CPC ........ *A61K 48/0058* (2013.01); *A61K 9/0048* (2013.01); *A61K 38/1709* (2013.01); *A61K 48/005* (2013.01); *A61K 48/0075* (2013.01); *C07K 14/47* (2013.01); *C12N 15/86* (2013.01); *A61K 38/00* (2013.01); *A61K 2039/515* (2013.01); *C12N 2750/14143* (2013.01); *C12N 2830/15* (2013.01)

(58) Field of Classification Search
CPC .............. A61K 2039/505; A61K 38/00; A61K 38/1709; A61K 48/005; A61K 48/0058; A61K 48/0075; A61K 9/0048; A61P 35/00; A61P 35/02; A61P 43/00; A61P 27/02; C07K 16/2803; C07K 16/2809; C07K 16/2866; C07K 16/2896; C07K 16/3061; C07K 2299/00; C07K 2317/21; C07K 2317/24; C07K 2317/31; C07K 2317/33; C07K 2317/34; C07K 2317/55; C07K 2317/565; C07K 2317/622; C07K 2317/92; C07K 2317/94; C07K 14/47; C12N 15/86; C12N 2750/14143; C12N 2830/15
USPC ........... 424/93.21, 93.7; 435/325, 375, 235.1
See application file for complete search history.

(56) References Cited

U.S. PATENT DOCUMENTS

| | | | |
|---|---|---|---|
| 5,139,941 | A | 8/1992 | Muzyczka et al. |
| 5,478,745 | A | 12/1995 | Samulski et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,629,322 | B2 | 12/2009 | Kleinschmidt et al. |
| 7,790,449 | B2 | 9/2010 | Gao et al. |
| 7,906,111 | B2 | 3/2011 | Wilson et al. |

(Continued)

FOREIGN PATENT DOCUMENTS

| | | |
|---|---|---|
| EP | 1310571 | 5/2003 |
| WO | WO 2003/042397 | 5/2003 |

(Continued)

OTHER PUBLICATIONS

Frost et al. Vis Neurosci. May 2013 ; 30(3): 55-64. (Year: 2013).*

(Continued)

*Primary Examiner* — Janet L Epps-Smith
(74) *Attorney, Agent, or Firm* — Howson and Howson LLP; Cathy Kodroff

(57) ABSTRACT

Engineered MREG proteins are described. Further described are viral vectors expressing native or engineered MREG proteins. Further described are compositions containing these vectors or proteins formulated for delivery to the eye. Also provided are methods for delivering these native and engineered MREG proteins to ocular cells for treatment of Stargardt's disease, macular degeneration and other ocular disorders.

7 Claims, 14 Drawing Sheets
Specification includes a Sequence Listing.

(56) References Cited

U.S. PATENT DOCUMENTS

| | | |
|---|---|---|
| 2007/0036760 A1 | 2/2007 | Wilson et al. |
| 2009/0197338 A1 | 8/2009 | Vandenberghe et al. |

FOREIGN PATENT DOCUMENTS

| | | | |
|---|---|---|---|
| WO | WO 2005/033321 | 4/2005 | |
| WO | WO 2005/107396 | 11/2005 | |
| WO | WO-2005107396 A2 * | 11/2005 | ............ A61P 43/00 |
| WO | WO 2006/110689 | 10/2006 | |
| WO | WO-2006130581 A2 * | 12/2006 | ............ C12N 15/85 |
| WO | WO 2011/126808 | 10/2011 | |
| WO | WO 2013/049493 | 4/2013 | |
| WO | WO 2015/012924 | 1/2015 | |

OTHER PUBLICATIONS

Kay et al. PLOS ONE, Apr. 2013 | vol. 8 | Issue 4; pp. 1-12. (Year: 2013).*

Dhingra A et al., Microtubule-Associated Protein 1 Light Chain 3B (LC3B) is Necessary to Maintain Lipid-Mediated Homeostasis in the Retinal Pigment Epithelim, 2018, Front. Cell Neurosci., 12: 352, epub Oct. 8, 2018.

Reyes-Reveles J et al., Phagocytosis-dependent ketogenesis in retinal pigment epithelium, 2017, J. Biol. Chem., 292(19):8038-8047, epub Mar. 16, 2017.

Sharp RC et al., Enhanced basal autophagy supports ameloblastoma-derived cell survival and reactivation, 2019, Arch. Oral Biol., 98:61-67, epub Nov. 14, 2018.

Beltran WA et al., rAAV2/5 gene-targeting to rods:dos-dependent efficiency and complications associated with different promoters, Gene Therapy, Sep. 2010; 17(9): 1162-74.

Buning H et al., Recent developments in adeno-associated virus vector technology, J. Gene Med, May 2008; 10(7):717-733.

Cai X et al., A 350 bp region of the proximal promoter of Rds drives cell-type specific gene expression, Exp Eye Res, Aug. 2010; 91(2):186-94.

Damek-Poprawa M et al., Melanoregulin (MREG) modulates lysosome function in pigment epithelial cells, Journal of Biological Chemistry, Apr. 17, 2009; 284(16):10877-89.

Dunaief JL et al., The role of apoptosis in age-related macular degeneration, Arch Opththalmol, Nov. 2002; 120(11):1435-42.

Fisher KJ et al. Transduction with recombinant adeno-associated virus for gene therapy is limited by leading-strand synthesis. J. Virol., Jan. 1996; 70:520-32.

Frost LS et al., Loss of melanoregulin (MREG) enhances cathepsin-D secretion by the retinal pigment epithelium, Vis. Neurosci., May 2013; 30(3):55-64. (Epub Apr. 23, 2013).

Frost LS et al., Putative role for melanoregulin (Mreg) in bisretinoid lipofuscin degradation in the retinal pigment epithelium (RPE), Investigative Ophthalmology & Visual Science, Mar. 2012; 53(14):6565.

Frost LS et al., The Contribution of Melanoregulin to Microtubule-Associated Protein 1 Light Chain 3 (LC3) Associated Phagocytosis by the Retinal Pigment Epithelium. Molecular Neurobiology, Dec. 2015; 52(3): 1135-51. (Epub Oct. 10, 2014).

Genbank Accession No. AY327580 (Jun. 2003).

Grieger JC and RJ Samulski, Adeno-associated virus as a gene therapy vector: Vector development, production and clinical applications, Adv. Biochem. Eng. Biotechnol., Oct. 2005; 99:119-45.

Kachi S et al., Equine infectious anemia viral vector-mediated codelivery of endostatin and angiostatin driven by retinal pigmented epithelium-specific VMD2 promoter inhibits choroidal neovascularization, Human Gene Therapy, Jan. 2009; 20(1):31-9.

Kazi AS et al., Loss of melanoregulin (MREG) may function as a possible risk factor for retinal degenerative diseases. Investigative Ophthalmology & Visual Science, Apr. 2010; 51(13):5977.

Lambard S et al., Expression of rod-derived cone viability factor: dual role of CRX in regulating promoter activity and cell-type specificity, PLoS One, Oct. 7, 2010; 5(10):e13025.

Mccarty DM et al., Self-complementary recombinant adeno-associated virus (scAAV) vectors promote efficient transduction independently of DNA synthesis, Gene Therapy, Aug. 2001; 8(16):1248-54.

Mclaughlin SK et al., Adeno-associated virus general trasnduction vectors: analysis of proviral structures, J. Virol., Jun. 1988, 62:1963-73.

Morrissey ME et al., PRE-1 a cis element sufficient to enhance cone- and rod-specific expression in differentiating zebrafish photoreceptors, BMC Dev Biol, Jan. 2011; 11(2): 12 pages.

Mussolino C et al., AAV-mediated photoreceptor transduction of the pig cone-enriched retina, Gene Therapy, Jul. 2011; 18(7):637-45.

Nicoud M et al., Development of photoreceptor-specific promoters and their utility to investigate EIAV lentiviral vector mediated gene transfer to photoreceptors, J Gene Med, Dec. 2007; 9(12):1015-23.

Shu X et al., Functional characterization of the human RPGR proximal promoter, Investigative Ophthalmology & Visual Science, Jun. 2012; 53(7):3951-8.

Thompson JD et al., A comprehensive comparison of multiple sequence alignments, Nucl. Acids. Res., Jul. 1, 1999; 27(13):2682-90.

Young JE et al., A short, highly active photoreceptor-specific enhancer/promoter region upstream of the human rhodopsin kinase gene, Investigative Ophthalmology & Visual Science, Sep. 2003; 44(9):4076-85.

Zhang H et al., Adenovirus-adeno-associated virus hybrid for large-scale recombinant adeno-associated virus production, Human Gene Therapy, Aug. 2009; 20:922-9.

International Search Report and Written Opinion issued in International Application No. PCT/US2016/055963, dated Dec. 28, 2016.

* cited by examiner

Mutants- MREG- W87A and MREG L90A.

pENN.AAV.CMV.PI.MREG.

415nm    Autofluorescent emission with excitation at 405nm

FIG 9A

| ID | Name | Clone # |
|---|---|---|
| DSMREGΔ10 | pGEXhMREGΔ10 | Clone #38 |
| DSMREG Δ20 | pGEXhMREGΔ20 | Clone#6 |
| DSMREG Δ30 | pGEXhMREGΔ30 | Clone#1 |
| USMREG Δ10 | pGEXhMREG-gstΔ10 | Clone#1 |
| USMREGΔ20 | pGEXhMREG-gstΔ20 | Clone #1 |
| USMREG Δ30 | pGEXhMREG-gstΔ30 | Clone#9 |

FIG 9B

5'-
TCATCTCAATCGGATCTGGTTCGCGTGGATCCCCGGGGCTGAGGGACTGGAAACAGTATTC
ATGGGGCTGAGGGACTGGCTGAGAACCGTGTGCTGCTGCTGCGGGTGCGAGTGCTTGGAG
GAGCGCGCCCTGCCTGAGAAGGAGCCCCTCGTCAGTGATAACAATCCATATTCCTCATTTG
GAGCAACTCTGGTGAGGGATGATGAGAAGAATTTATGGAGTATGCCCCATGATGTGTCCC
ACACAGAGGCAGACGACGACAGAACCCTGTACAATTTGATAGTCATTCGTAATCAGCAGGC
CAAAGACTCAGAGGAGTGGCAGAAGCTCAACCATGATATCCATACCCTGCGGCAGGTTCGA
AGGGAAGTAAGAAACAGATGGAAGTGCATCTTAGAAGATTTAGGTTTTCAAAAGGAAGCT
GACTCTTTGTTGTCAGTGACTAAACTCAGCACCATCAGTGATTCTAAAAACACAAGGAAAG
CTCGAGAGATGTTGTTAAAACTGGCTGAAGAAACCAATATTTTCCCAACAAGTTGGGAGCT
CTCAGAGAGATATCTCTTTGTTGTGGACCGTCTCATTGCACTTGATGCTGCAGAGGAGTTC
TTTAAGCTTGCTCGTCGAACTTACCCCAAGAAGCCTGGGGTTCCATGCCTGGCAGATGGCC
AGAAATAACTGCACTACCTTCCGTTTCCAAGTCCCGGGAATTCATCGTGACTGACTGACGA
TCTGCCTCGCGCGTTTCGGTGATGACGGTGAAAACCTCTGACACATGCAGCTCCCGGAGAC
GGTCACAGCTTGTCTGTAAGCGGATGCCGGGAGCAGACAGCCCGTCAGGCGCGTCAGCGG
TGTTGGCGGTGTCGGGGCGCAGCCATGACCCAGTCACGTAGCGAWTAGCGGAGTGTATAA
A-3'

FIG. 9C

DS MREGΔ20 (pGEXhMREGΔ20,Clone#6)

5'-
GGTGATCATTAAGCCATCATGACGTCAGATGTATGCTCTTGATGTGTTGTATACATGACCC
ATGTGCCTGGATGCGTCCAAATGTTGTTTAAAAAACGTATTGAAGCTTCCACAAATTGATA
AGTACTTGAATCCAGCAAGTATATAGCATGGCCTTTGCAGGCTGGCAAGCCACGTTTGGTG
GTGTGACCATCATCCAAAATCGGATCTGGTTCCGGTGGATCCCCGGGGCTGAGGGACTGG
AAACAGTATTC<u>ATGGGGCTGAGGGACTGGCTGAGAACCGTGTGCTGCTGCTGCGGGTGCG</u>
<u>AGTGCTTGGAGGAGCGCGCCCTGCCTGAAGGAGCCCCTCGTCAGTGATAACAATCCAT</u>
<u>ATTCCTCATTTGGAGCAACTCTGGTGAGGGATGATGAGAAGAATTTATGGAGTATGCCCCA</u>
<u>TGATGTGTCCCACACAGAGGCAGACGACGACAGAACCCTGTACAATTTGATAGTCATTCGT</u>
<u>AATCAGCAGGCCAAAGACTCAGAGGAGTGGCAGAAGCTCAACCATGATATCCATACCCTGC</u>
<u>GGCAGGTTCGAAGGGAAGTAAGAAACAGATGGAAGTGCATCTTAGAAGATTTAGGTTTTC</u>
<u>AAAAGGAAGCTGACTCTTTGTTGTCAGTGACTAAACTCAGCACCATCAGTGATTCTAAAAA</u>
<u>CACAAGGAAAGCTCGAGAGATGTTGTTAAAACTGGCTGAAGAAACCAATATTTTCCCAACA</u>
<u>AGTTGGGAGCTCTCAGAGAGATATCTCTTTGTTGTGGACCGTCTCATTGCACTTGATGCTG</u>
<u>CAGAGGAGTTCTTTAAGCTTGCTCGTCGAACTTACCCCAAGAAGCC</u>TAAGTTCCATGCCT
GGCAGATGGCCAGAAATAACTGCACTACCTTCCGTTTCCAAGTCCCGGGAATTCATCGTGA
CTGACTGACGATCTGCCTCGCGCGTTCGAA-3'

FIG 9D

DS MREGΔ30 (pGEXhMREGΔ30,Clone#1)

5'-
GYCCAATCTCAAATCGGATCTGGTTCCGCGTGGATCCCCGGGGCTGAGGGACTGGAAACAG
TATTC<u>ATGGGGCTGAGGGACTGGCTGAGAACCGTGTGCTGCTGCTGCGGGTGCGAGTGCTT</u>
<u>GGAGGAGCGCGCCCTGCCTGAAGGAGCCCCTCGTCAGTGATAACAATCCATATTCCTCAT</u>
<u>TTGGAGCAACTCTGGTGAGGGATGATGAGAAGAATTTATGGAGTATGCCCCATGATGTGTC</u>
<u>CCACACAGAGGCAGACGACGACAGAACCCTGTACAATTTGATAGTCATTCGTAATCAGCAG</u>
<u>GCCAAAGACTCAGAGGAGTGGCAGAAGCTCAACCATGATATCCATACCCTGCGGCAGGTTC</u>
<u>GAAGGGAAGTAAGAAACAGATGGAAGTGCATCTTAGAAGATTTAGGTTTTCAAAAGGAAGC</u>
<u>TGACTCTTTGTTGTCAGTGACTAAACTCAGCACCATCAGTGATTCTAAAAACACAAGGAAAG</u>
<u>CTCGAGAGATGTTGTTAAAACTGGCTGAAGAAACCAATATTTTCCCAACAAGTTGGGAGCTC</u>
<u>TCAGAGAGATATCTCTTTGTTGTGGACCGTCTCATTGCACTTGATGCTGCAGAAGAGTTCTT</u>
<u>TAAG</u>TAAGCTCGTCGAACTTACCCCAAGAAGCCTGGGGTTCCATGCCTGGCAGATGGCCAG
AAATAACTGCACTACCTTCCGTTTCCAAGTCCCGGGAATTCATCGTGACTGACTGACGATCT
GCCTCGCGCGTTTCGGTGATGACGGTGAAAACCTCTGACACATGCAGCTCCCGGAGACGGT
CACAGCTTGTCTGTAAGCGGATGCCGGGAGCAGACAAGCCCGTCAGGCGCGTCAGCGGGTG
TTGGCGGGTGTCGGGGCGCAGCCATGACCCAGTCACGTAGCGATAGCGGAGTGTATAAATT
CTTGAAGRACG-3'

FIG 9E

USMREGΔ10 (pGEXhMREG-gstΔ10, Clone #1)

5'-
ACTGCACGGTGCACCAATGCTTCTGGCGTCAGGCAGCCATCGAAGCTGTGGTATGCTGTGC
AGGTCGTAAATCACTGCATAATTCGTGTCGCTCAAGGCGCACTCCCGTTCTGGATAATGTTT
TTTGCGCCGACATCATAACGGTTCTGGCAAATATTCTGAAATGAGCTGTTGACAATTAATCA
TCGGCTCGTATAATGTGTGGAATTGTGAGCGGATAACAATTTCACACAGGAAACAGTATTC
ATGGGGCTGAGGGACTGGAAACAGTATTC<u>ATGGGGCTGAGGGACTGGCTGAGAACCGTGT
GCTGCTGCTGCGGGTGCGAGTGCTTGGAGGAGCGCGCCCTGCCTGAGAAGGAGCCCCTCG
TCAGTGATAACAATCCATATTCCTCATTTGGAGCAACTCTGGTGAGGGATGATGAGAAGAA
TTTATGGAGTATGCCCCATGATGTGTCCCACACAGAGGCAGACGACGACAGAACCCTGTAC
AATTTGATAGTCATTCGTAATCAGCAGGCCAAAGACTCAGAGGAGTGGCAGAAGCTCAACT
ATGATATCCATACCCTGCGGCAGGTTCGAAGGGAAGTAAGAAACAGATGGAAGTGCATCTT
AGAAGATTTAGGTTTTCAAAAGGAAGCTGACTCTTTGTTGTCAGTGACTAAACTCAGCACC
ATCAGTGATTCTAAAAACACAAGGAAAGCTCGAGAGATGTTGTTAAAACTGGCTGAAGAAA
CCAATATTTTCCCAACAAGTTGGGAGCTCTCAGAGAGATATCTCTTTGTTGTGGACCGTCTC
ATTGCACTTGATGCTGCAGAGGAGTTCTTTAAGCTTGCTCGTCGAACTTACCCCAAGAAGCC
TGGGGTTCCATGCCTGGCAGATGGCCAGACCATGGCCCCTATACTAGGTTATTGGAAAAT
AAGGGCCTGTGCAACCCACTCGAT</u>-3'

FIG. 9F

USMREGΔ20 (pGEXhMREG-gstΔ20, Clone #1)

5'-
TSTTACATTTCCACAGGAACAGTATTCATGGGGCTGAGGGACTGGAAACAGTATTC<u>ATGGG
GCTGAGGGACTGGCTGAGAACCGTGTGCTGCTGCTGCGGGTGCGAGTGCTTGGAGGAGCG
CGCCCTGCCTGAGAAGGAGCCCCTCGTCAGTGATAACAATCCATATTCCTCATTTGGAGCAA
CTCTGGTGAGGGATGATGAGAAGAATTTATGGAGTATGCCCCATGATGTGTCCCACACAGA
GGCAGACGACGACAGAACCCTGTACAATTTGATAGTCATTCGTAATCAGCAGGCCAAAGAC
TCAGAGGAGTGGCAGAAGCTCAACTATGATATCCATACCCTGCGGCAGGTTCGAAGGGAAG
TAAGAAACAGATGGAAGTGCATCTTAGAAGATTTAGGTTTTCAAAAGGAAGCTGACTCTTT
GTTGTCAGTGACTAAACTCAGCACCATCAGTGATTCTAAAAACACAAGGAAAGCTCGAGAG
ATGTTGTTAAAACTGGCTGAAGAAACCAATATTTTCCCAACAAGTTGGGAGCTCTCAGAGA
GATATCTCTTTGTTGTGGACCGTCTCATTGCACTTGATGCTGCAGAGGAGTTCTTTAAGCTT
GCTCGTCGAACTTACCCCAAGAAGCCCATGGTTCCATGCCTGGCCAAGAAGCCCATGGTT
CCATGCCTGGCAGATGGCCAGAAAGAACTGCACTACCTTCCGTTTCCAAGTCCCATGGCCCC
TATACTAGGTTATTGGAAAATTAAGGGCCTTGTGCAACCCACTCGACTTCTTTTGGAATATC
TTGAAGAAAAATATGAAGAGCATTTGTATGAGCGCGATGAAGTGATAATGGCGAAACAAAA
AGTTGATGGTTGGAGTTCCATCTCTATATATGATGGTGATGTAATTAACACAGTCTATGGCC
ATCAT</u>-3'

FIG 9G

USMREGΔ30 (pGEXhMREG-gstΔ30, Clone #1)

5'-
TGTTGATGAAAGCTGGCTACAGGAAGGCCCAGACGCGAATTATTTTTGATGCGTGGAATTA
GCTATCGACTGCACGGTGCACCAATGCTTCTGGCGTCAGGCAGCCATCGGAAGCTGTGGTA
TGGCTGTGCAGGTCGTAAATCACTGCATAATTCGTGTCGCTCAAGGCGCACTCCCGTTCTG
GATAATGTTTTTTGCGCCGACATCATAACGGTTCTGGCAAATATTCTGAAATGAGCTGTTG
ACAATTAATCATCGGCTCGTATAATGTGTGGAATTGTGAGCGGATAACAATTTCACACAGG
AAACAGTATTCATGGGGCTGAGGGACTGGAAACAGTATTC<u>ATGGGGCTGAGGGACTGGCT
GAGAACCGTGTGCTGCTGCTGCGGGTGCGAGTGCTTGGAGGAGCGCGCCCTGCCTGAGAA
GGAGCCCCTCGTCAGTGATAACAATCCATATTCCTCATTTGGAGCAACTCTGGTGAGGGAT
GATGAGAAGAATTTATGGAGTATGCCCCATGATGTGTCCCACACAGAGGCAGACGACGAC
AGAACCCTGTACAATTTGATAGTCATTCGTAATCAGCAGGCCAAAGACTCAGAGGAGTGGC
AGAAGCTCAACTATGATATCCATACCCTGCGGCAGGTTCGAAGGGAAGTAAGAAACAGAT
GGAAGTGCATCTTAGAAGATTTAGGTTTTCAAAAGGAAGCTGACTCTTTGTTGTCAGTGAC
TAAACTCAGCACCATCAGTGATTCTAAAAACACAAGGAAAGCTCGAGAGATGTTGTTAAAA
CTGGCTGAAGAAACCAATATTTTCCCAACAAGTTGGGAGCTCTCAGAGAGATATCTCTTTG
TTGTGGACCGTCTCATTGCACTTGATGCTGCAGAAGAGTTCTTTACCATGGCCCCTATACT
AGGTTATTGGAAAATTAAGGGCCTGTGCAACCCACTCGAAT</u>-3'

FIG 9H

Primer Table

| ID | | Sequence |
|---|---|---|
| DS MREG<br>DSMREGΔ10 | F | GGGCTGGCAAGCCACGTTTGGTG |
| DSMREG Δ20<br>DSMREG Δ30 | R | CCGGGAGCTGCATGTGTCAGAGG |
| US MREG<br>USMREG Δ10 | F | CATCGGCTCGTATAATGTGT |
| USMREGΔ20<br>USMREG Δ30 | R | CCGGGAGCTGCATGTGTCAGAGG |

FIG 10A

| ID/Name | Clone # |
| --- | --- |
|  |  |
| GFP-MREG (W87A) | 1010 |
| MREG-GFP (W87A) | 1017 |
| GFP-MREG (L90A) | 1019 |
| MREG-GFP (L90A) | 1018 |

FIG 10B

Species: Mus musculus

Primers (N-terminal GFP):

| Forward | AGCTTCCCGACTACCACT |
| --- | --- |
| Reverse | CAGTGCAGTTTTCTCTGGC |

Primers (C-terminal GFP):

| Forward | No mutation-spanning forward primer |
| --- | --- |
| Reverse | ATCCTGGGGCTTGGAAAT |

FIG. 10C

5'-
ATGGGGCTGCGCCGCTGGCTACGGAGCGCCTGCTGCTGCTGCCCGTGCCGGTGCCTGGAG
GAGCCCGCGCGGCCCGAGAAGGAGCCGCTGGTCAGTGGTAACAATCCGTATTCCTCCTTT
GGAGCGACTCTGGAGAGGGATGATGAGAAGAATTTATGGAGCATGCCTCATGACGTGTC
CCACACAGAGGCGGATGACGATAGGATCTTGTATAATTTGATAGTCATTCGTAATCAGCA
GACCAAAGACTCAGAGGAATGGCAAAGA<u>GCC</u>AACTATGATATCTACACCCTGCGGCAGA
TCCGCAGGGAAGTGAGGAACCGATGGAGACGAATCTTAGAGGACTTGGGCTTTCAAAGG
GAAGCCGACTCTCTGTTGTCAGTGACCAAACTCAGCACCATGAGTGATTCTAAAAACACA
AGGAAAGCCCGGGAGATGCTGTTAAAGCTGGCTGAAGAGACCTCTATCTTCCCCGCCAG
CTGGGAGCTCTCCGAGAGGTACCTCTTGGTTGTGGACCGGCTCATTGCTCTCGATGCTGC
TGAGGACTTCTTTAAGATTGCTAGCCAAATGTACCCCAAGAAACCTGGGGTCCCATGCCT
GGTGGACGGCCAGAGAAAACTGCACTGCCTTCCATTTCCAAGCCCC-3'

FIG 10D

Species: Mus musculus
Primers (N-terminal GFP):

| Forward | AGCTTCCCGACTACCACT |
|---------|--------------------|
| Reverse | CAGTGCAGTTTTCTCTGGC |

Primers (C-terminal GFP):

| Forward | No mutation-spanning forward primer |
|---------|-------------------------------------|
| Reverse | ATCCTGGGGCTTGGAAAT |

FIG 10E

5'-
ATGGGGCTGCGCCGCTGGCTACGGAGCGCCTGCTGCTGCTGCCCGTGCCGGTGCC
TGGAGGAGCCCGCGCGGCCCGAGAAGGAGCCGCTGGTCAGTGGTAACAATCCGT
ATTCCTCCTTTGGAGCGACTCTGGAGAGGGATGATGAGAAGAATTTATGGAGCAT
GCCTCATGACGTGTCCCACACAGAGGCGGATGACGATAGGATCTTGTATAATTTG
ATAGTCATTCGTAATCAGCAGACCAAAGACTCAGAGGAA<u>GCG</u>CAAAGACTCAAC
TATGATATCTACACCCTGCGGCAGATCCGCAGGGAAGTGAGGAACCGATGGAGA
CGAATCTTAGAGGACTTGGGCTTTCAAAGGGAAGCCGACTCTCTGTTGTCAGTGA
CCAAACTCAGCACCATGAGTGATTCTAAAAACACAAGGAAAGCCCGGGAGATGC
TGTTAAAGCTGGCTGAAGAGACCTCTATCTTCCCCGCCAGCTGGGAGCTCTCCGA
GAGGTACCTCTTGGTTGTGGACCGGCTCATTGCTCTCGATGCTGCTGAGGACTTC
TTTAAGATTGCTAGCCAAATGTACCCCAAGAAACCTGGGGTCCCATGCCTGGTGG
ACGGCCAGAGAAAACTGCACTGCCTTCCATTTCCAAGCCCC-3'

US 11,273,227 B2

COMPOSITIONS AND METHODS USEFUL IN TREATING STARGARDT'S DISEASE AND OTHER OCULAR DISORDERS

STATEMENT OF FEDERALLY SPONSORED RESEARCH

This work was supported by Public Health Service Grant EY-10420 awarded by the National Institutes of Health. The US government may have certain rights in this invention.

BACKGROUND OF THE INVENTION

Macular degeneration is a genetic eye disorder that affects the retina resulting in progressive vision loss. It is the most common form of juvenile macular degeneration, the symptoms of which begin in early childhood. The estimated prevalence of Stargardt macular degeneration is 1 in 8,000 to 10,000 individuals. Specifically, this form of macular degeneration affects an area near the center of the retina that is responsible for sharp central vision. This area, termed the macula, is required for detailed tasks such as facial recognition, reading, cooking and driving. In addition to central vision loss, people with Stargardt's often have compromised night vision making it difficult to navigate in low light. A clinical hallmark of Stargard's, is the buildup of a fatty yellow pigment called lipofuscin in cells underlying the macula. Over time, the abnormal accumulation of this substance can damage cells that are critical for clear central vision.

The ATP-binding cassette, sub-family A (ABC1), member 4 ABCA4 protein transports potentially toxic substances out of photoreceptor cells. Mutations in ABCA4 gene are known to cause the autosomal-recessive disease Stargardt macular dystrophy (STGD) 1, which is a hereditary juvenile macular degeneration disease causing progressive loss of photoreceptor cells. STGD is characterized by reduced visual acuity and color vision, loss of central (macular) vision and accumulation of autoflourescent RPE debris. This autofluorescent debris includes both lipid and protein components. On a molecular level, mutations in the ABCA4 gene prevent the ABCA4 protein from removing toxic by-products from photoreceptor cells. These toxic substances build up and form lipofuscin in the RPE, eventually causing cell death, with degeneration of photoreceptors likely secondary to the loss of the RPE. Lipofuscin is a complex mix of compounds composed of lipid-containing residues of lysosomal digestion.

What are needed are compositions and methods useful in treating the symptoms of ocular disorders, including Stargardt's disease.

SUMMARY OF THE INVENTION

In one embodiment, a composition is described which comprises an engineered nucleic acid molecule useful in the treatment of a subject having age-related macular degeneration and/or Stargardt's Disease comprising a sequence encoding a melanoregulin (MREG) under the control of expression control sequences which direct expression thereof in ocular cells; and a carrier suitable for delivery to the eye of the subject. In one embodiment, an engineered MREG is utilized. In another aspect, an engineered MREG protein is provided.

In one embodiment, the engineered nucleic acid is packaged in a viral vector. Thus, in one aspect, a recombinant adeno-associated viral (rAAV) vector is provided which is useful in treating a subject with age-related macular degeneration and/or Stargardt's Disease. The rAAV comprises an AAV capsid having packaged therein: a 5' AAV inverted terminal repeat (ITR) sequence, a sequence encoding melanoregulin (MREG) under the control of expression control sequences which direct expression thereof in ocular cells, and a 3' AAV.

In a further embodiment, use of a nucleic acid, protein, or viral vector as described herein for treating Stargardt's Disease is provided.

In still another embodiment, use of a nucleic acid, protein, or viral vector as described herein for treating macular degeneration is provided.

Still other aspects and advantages of the invention will be apparent from the following detailed description of the invention.

BRIEF DESCRIPTION OF THE DRAWINGS

FIG. 1A is a schematic representation of MREG dependent LC3 associated degradation of debris (phagosomes are illustrated) in the RPE. The association between MREG and the autophagy protein, Microtubule associated protein Light chain 3, (LC3) is involved in the tagging of phagosomes or intracellular debris for degradation by lysosomes in a process known as LC3 associated phagocytosis. FIG. 1B is a schematic representation of human MREG with the palmitylation sites between residues 10 and 20 and sequence highlighted in gray.

FIG. 3A is quantitation of levels of MREG protein in RPE of mice, either un-injected designated C, injected with vehicle control, designated $C_i$ or with MREG pENN.AAV.CMV.PI.MREG.SV40 (p1690), designated $M_i$. Mice were sacrificed and RPE lysates analyzed at the ages indicated. MREG expression was stable for 10 months. The MREG binding partner was also analyzed in these samples and found to remain relatively constant suggesting no off target effects. FIG. 3B is quantitation of MREG levels based on densitometric analysis of images in FIG. 3A normalized to actin at the ages indicated.

FIGS. 6A-6D show that increased MREG decreases intracellular cholesterol accumulation. FIGS. 6A-6B are panels showing cholesterol levels indicated as filipin positive structures in RPE from ABCA4−/− mice injected with pEN-N.AAV.CMV.PI.hMREG.SV40, labeled MREG Inj compared to vehicle controls, designated Ctrl Inj. Whole mounts prepared from ABCA4−/− mice (8 months old, 3 h after light onset) were analyzed for cholesterol, using filipin staining. Cholesterol puncta are indicated by arrows. The percent decrease in cholesterol based on fluorescence imaging (decrease 485%) is indicated. RPE=Retinal Pigment Epithelium. Scale bar=10 μm. FIGS. 6C-6D are eyecup preparations from Ctrl injected and MREG-injected mouse retinal/RPE sections were analyzed for cholesterol, using filipin staining. Cholesterol puncta are indicated by arrows. The percent decrease in cholesterol based on fluorescence imaging is indicated (209% decrease). RPE=Retinal Pigment Epithelium. Scale bar=5 μm.

FIG. 9A is a table providing the MREG deletion clones. The nucleic acid sequences of these clones follows in FIGS. 9B-9G.

FIG. 9B provides the nucleic acid sequence of DS MREG Δ10 (pGEXhMREGΔ10, Clone #38) [SEQ ID NO: 6]. All sequencing data provided is from the forward direction. The translated regions are shown by double underline [SEQ ID NO: 7, 8]. Mutation sites are identified by single underlining and bold.

FIG. 9C provides the nucleic acid sequence of DS MREGΔ20 (pGEXhMREGΔ20, Clone #6) [SEQ ID NO: 51]. All sequencing data provided is from the forward direction. The translated regions are shown by double underline [SEQ ID NO: 52, 53, 54]. Mutation sites are identified by single underlining and bold.

FIG. 9D provides the nucleic acid sequence of DS MREGΔ30 (pGEXhMREGΔ30, Clone #1) [SEQ ID NO: 9]. All sequencing data provided is from the forward direction. The translated regions are shown by double underline [SEQ ID NO: 10, 11, 12]. Mutation sites are identified by single underlining and bold.

FIG. 9E provides the nucleic acid sequence of USMREGΔ10 (pGEXhMREG-gstΔ10, Clone #1) [SEQ ID NO: 13]. All sequencing data provided is from the forward direction. The translated regions are shown by double underline [SEQ ID NO: 14, 15, 16, 17, 18, 19, 20, 21, 22, 23, 24, 25, 26]. Mutation sites are identified by single underlining and bold.

FIG. 9F provides the nucleic acid sequence of USMREGΔ20 (pGEXhMREG-gstΔ20, Clone #1) [SEQ ID NO:31]. All sequencing data provided is from the forward direction. The translated regions are shown by double underline [SEQ ID NO: 32, 33, 34]. Mutation sites are identified by single underlining and bold.

FIG. 9G provides the nucleic acid sequence of USMREGΔ30 (pGEXhMREG-gstΔ30, Clone #1) [SEQ ID NO: 35]. The translated regions are shown by double underline [SEQ ID NO: 36].

FIG. 9H provides a primer table for the clones in FIGS. 9A-9 G. The forward primer for the DS clones is provided in SEQ ID NO: 37. The reverse primer for the DS clones is provided in SEQ ID NO: 38. The forward primer for the US clones is provided in SEQ IDNO: 39. The reverse primer for the US clones is provide in SEQ ID NO: 40.

FIG. 10A provides a table identifying the MREG-LC3 interacting region (LIR) mutants). Primers for generating these mutants and sequences are provided in FIGS. 10B-10E.

FIG. 10B provides a table of the GFP-MREG (L90) Clone #1019 and MREG-GFP (L90A) Clone #1018 primers used to generate the L90A mutation on murine MREG. For *Mus musculus*, the forward N-terminal GFP primer is provided in SEQ ID NO: 41; the reverse N-terminal GFP primer is provided in SEQ ID NO: 42; the reverse primer for the C-terminal GFP is provided in SEQ ID NO: 43.

FIG. 10C provides the nucleic acid sequence of the L90A mutation on mMREG (double underline) [SEQ ID NO: 44]. The translated sequence is provided in SEQ ID NO: 45.

FIG. 10D provides the primers used for GFP-MREG (W87A) Clone #1010 and MREG-GFP (W87A) Clone #1017. For *Mus musculus*, the forward N-terminal GFP primer is reproduced in SEQ ID NO: 46 and the reverse N-terminal GFP primer is reproduced in SEQ ID NO: 47. The C-terminal reverse primer is reproduced in SEQ ID NO: 48.

FIG. 10E provides the nucleic acid sequence of the W87A Mutation on mMREG (double underline) [SEQ ID NO: 49]. The translated sequence is provided in SEQ ID NO:50.

DETAILED DESCRIPTION OF THE INVENTION

Figure 1A:
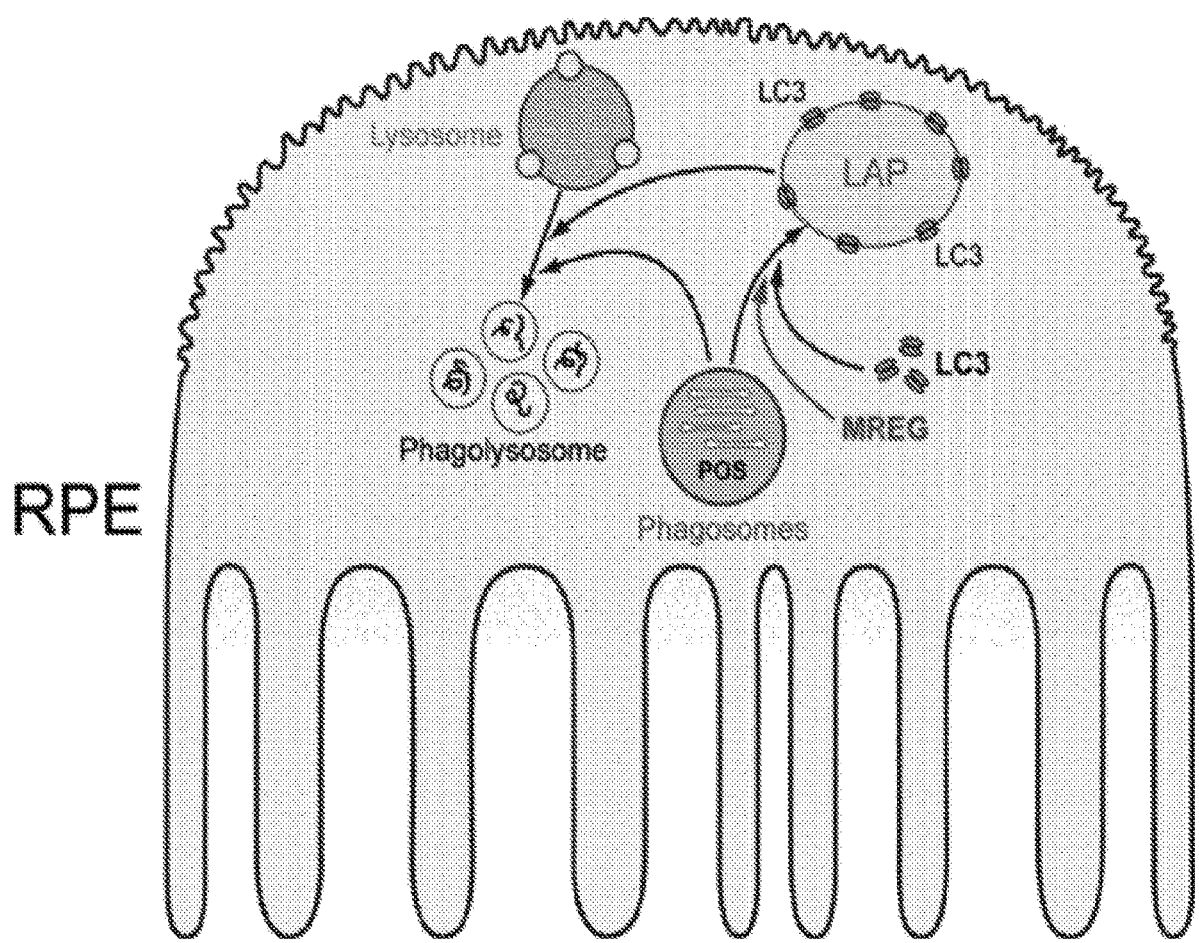
FIGS. 1A-1B are schematic representations.

The novel viral vectors carrying an MREG protein and the novel engineered mutant MREG proteins described herein are useful for treating the symptom associated with Stargardt's Disease. Delivery of these vectors and mutants to subjects in need thereof via a number of routes, and particularly by expression in vivo mediated by a recombinant vector such a rAAV vector, are described. Also provided are methods of using these variants in regimens for treating ocular disorders, including, without limitation, a multifactorial ocular disorder in a human subjects characterized by lipofusconesis, production of 7-keto-cholesterol, a toxic component of RPE lipid debris which activates the RPE inflammasome, and/or oxidized lipid adducts.

As used herein, the term "MREG" refers to melanoregulin, which is also known as dilute suppressor protein homolog (DSU). As used herein the "wild-type" human MREG is isoform 1, which is characterized by the amino acid sequence:

```
SEQ ID NO: 55:
MGLRDWLRTV CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKPGVPCLA

DGQKELHYLP FPSP.
```

Isoform 2 of MREG differs from the above sequence at amino acids 208-214 (with reference to SEQ ID NO:55), in which

```
            (see, aa 208-224 of SEQ ID NO: 56)
            YLPFPSP → LWGDLSCRLAHMQGVLH.
```

Human MREG, isoform 2, has the sequence:

```
SEQ ID NO: 56:
MGLRDWLRTV CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKPGVPCLA

DGQKELHL NVGDLSCRLAHMQGVLH.
```

A naturally occurring variant of these sequences has been described, in which amino acid position 15 (based on the wild-type) is changed from a G to an R. Encompassed within the MREGs are modified MREG proteins having at least 95% identity to the sequences above and the same function as isoform 1 and/or isoform 2.

The term "amino acid substitution" and its synonyms described above are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

As used throughout the specification, the term "a MREG" encompasses both these isoforms and the naturally occurring variants which are functional MREG proteins, as well as the engineered mutants provided herein, unless otherwise specified.

As used herein, exemplary engineered mutant MREG proteins include the following, shown from amino ($^N$)- to carboxy ($^C$)-terminus.

(a) MREG USΔ10:
[SEQ ID NO: 57]
```
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKPGVPCLA

DGQKELHYLP FPSP-$^C$:,
```

(b) MREG USΔ20:
[SEQ ID NO: 58]
```
$^N$-ERALPEKEPL VSDNNPYSSF GATLVRDDEK

NLWSMPHDVS HTEADDDRTL YNLIVIRNQQ AKDSEEWQKL

NYDIHTLRQV RREVRNRWKC ILEDLGFQKE ADSLLSVTKL

STISDSKNTR KAREMLLKLA EETNIFPTSW ELSERYLFVV

DRLIALDAAE EFFKLARRTY PKKPGVPCLA DGQKELHYLP

FPSP-$^C$,
```

(c) MREG USΔ30:
[SEQ ID NO: 59]
```
$^N$-VSDNNPYSSF GATLVRDDEK NLWSMPHDVS

HTEADDDRTL YNLIVIRNQQ AKDSEEWQKL NYDIHTLRQV

RREVRNRWKC ILEDLGFQKE ADSLLSVTKL STISDSKNTR

KAREMLLKLA EETNIFPTSW ELSERYLFVV DRLIALDAAE

EFFKLARRTY PKKPGVPCLA DGQKELHYLP FPSP-$^C$,
```

(d) MREG DSΔ10:
[SEQ ID NO: 60]
```
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKPGVPCLA

DGQK-$^C$,
```

(e) MREG DSΔ20:
[SEQ ID NO: 61]
```
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE
```

```
ADSLLSVTKL STISDSKNTR KAREMLLKLA EETNIFPTSW

ELSERYLFVV DRLIALDAAE EFFKLARRTY PKKP-C,
and (f) MREG DSΔ30:
                                    [SEQ ID NO: 62]
N-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFK-C.
```

These mutants contain deletions of about 10 to 30 amino acids in the N-terminus. C-terminus, and/or internally within the MREG isoform 1 protein sequence. It will be understood that one of these N-terminus or C-terminus truncations may be combined with shorter truncations in the other region, or internally, e.g., a 10 amino acid N-terminal truncation may be combined with a 1, 2, 3, to less than 10 amino acid C-terminal truncation, as compared to the MREG isoform 1. Conversely, an MREG mutant may have a 10 amino acid C-terminal truncation may be combined with a less than 10 amino acid truncation at the N-terminus, as compared to the wild-type MREG. Similar mutations may be made in the MREG isoform or variants thereof.

These MREG proteins, and the engineered mutants thereof, may be used to generate antibodies useful for a variety of purposes, including, e.g., monitoring therapy, purification, and the like. Thus, the invention further encompasses anti-MREG antibodies, which are optionally bound to a solid support, and further optionally, with a detectable label. Also provided are solid supports and kits containing these components.

Further encompassed by the invention are nucleic acid sequences encoding these MREG proteins, which may be selected for use in a nucleic acid molecule used to express these proteins, directly or via a vector. The nucleic acid coding sequences may be the wild-type sequences (see, FIGS. 9A-9H), or modified (see, FIGS. 10A-10E), e.g., optimized for human expression. Codon-optimized coding regions can be designed by various different methods. This optimization may be performed using methods which are available on-line, published methods, or a company which provides codon optimizing services. One codon optimizing method is described, e.g., in US Patent Application No. PCT/U.S. Ser. No. 14/35880 (WO 2015/012924), which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide. The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "Stargardt's Disease" refers to an autosomal recessive disease which is a common form of inherited juvenile macular degeneration (associated with ABCA4 mutation) and is sometimes known as Stargardt macular dystrophy or fundus flavimaculatus. The disease is associated with deposits of lipfuscin, a fatty byproduct of formal cell activity, which accumulated abnormally in the retinal pigment epithelium (RPE) and causes one or more of, bread down of the RPE, rods and/or cones, decreased color perception, loss of visual acuity, and blindness. A related condition, Stargardt macular degeneration, is associated with mutations in the ELOVL4. Current treatments are inadequate, but may include intraocular injections of anti-VEGF drugs, and nutrition (avoidance of excess levels of Vitamin A) and eye protection.

As used herein, "treatment" of an ocular disorder, including, e.g., Stargardt's Disease or Stargardt's macular degeneration, includes, e.g., slowing or stabilization of loss of visual acuity, slowing or stabilization of accumulation of lipfuscin, stabilization of the RPE, rods, and cones. In some instances, reversal of these symptoms is observed following treatment using a composition as described herein.

As used herein, the term "ocular cells" refers to any cell in, or associated with the function of, the eye. The term may refer to any one of photoreceptor cells, including rod, cone and photosensitive ganglion cells or retinal pigment epithelium (RPE) cells. In one embodiment, the ocular cells are the photoreceptor cells.

Nucleic Acid Molecules

The MREG proteins, including the engineered MREG proteins provided herein, may be expressed in vitro using any suitable production system for formulation with suitable carriers (e.g., saline, liposomes, etc), excipients, preservatives, or the like in a compositions. However, the proteins are particularly well suited for expression in vivo from a nucleic acid molecule, e.g., such as may be delivered by a viral vector.

In one embodiment, the nucleic acid sequences encoding the MREG protein described herein are engineered into any suitable genetic element, e.g., naked DNA, phage, transposon, cosmid, episome, etc., which transfers the MREG sequences carried thereon to a host cell, e.g., for generating non-viral delivery systems (e.g., RNA-based systems, naked DNA, or the like) or for generating viral vectors in a packaging host cell and/or for delivery to a host cells in subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, an "expression cassette" refers to a nucleic acid molecule which comprises the MREG coding sequences, promoter, and may include other regulatory sequences therefor, which cassette may be engineered into a genetic element and/or packaged into the capsid of a viral vector (e.g., a viral particle). Typically, such an expression cassette for generating a viral vector contains the MREG sequences described herein flanked by packaging signals of the viral genome and other expression control sequences such as those described herein.

The promoter may be a constitutive promoter (e.g., human cytomegalovirus promoter) or a tissue specific promoter, e.g., a retinal pigmented epithelium (RPE) promoter or a photoreceptor promoter. The promoter may be derived from any species. In another embodiment, the promoter is the human G-protein-coupled receptor protein kinase 1 (GRK1) promoter (Genbank Accession number AY327580). In another embodiment, the promoter is a 292 nt fragment (positions 1793-2087) of the GRK1 promoter (see also, Beltran et al, Gene Therapy 2010 17:1162-74, which is hereby incorporated by reference herein). In another preferred embodiment, the promoter is the human interphotoreceptor retinoid-binding protein proximal (IRBP) promoter. In another embodiment, promoter is the native promoter for the gene to be expressed. In one embodiment, the promoter is the RPGR proximal promoter (Shu et al, IOVS, May 2012, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Examples of photoreceptor specific promoters include, without limitation, the rod opsin promoter, the red-green opsin promoter, the blue opsin promoter, the inter photoreceptor binding protein (IRBP) promoter and the cGMP-β-phosphodiesterase promoter. In one embodiment, the promoter is of a small size, under 1000 bp, due to the size limitations of the AAV vector. In another embodiment, the promoter is under 400 bp.

In addition to a promoter, an expression cassette may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., CMV enhancer.

These control sequences are "operably linked" to the MREG gene sequences. As used herein, the term "operably linked" refers to both expression control sequences that are contiguous with the gene of interest and expression control sequences that act in trans or at a distance to control the gene of interest.

The expression cassette may be engineered onto a plasmid which is used for drug delivery or for production of a viral vector. Suitable viral vectors are preferably replication-defective and selected from amongst those which target ocular cells. Viral vectors may include any virus suitable for gene therapy may be used, including but not limited to adenovirus; herpes virus; lentivirus; retrovirus; parvovirus, etc.

Suitably, where one of these vectors is generated, it is produced as a replication-defective viral vector. A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In one embodiment, the viral vector is an adeno-associated virus (AAV). An adeno-associated virus (AAV) viral vector is an AAV DNase-resistant particle having an AAV protein capsid into which is packaged nucleic acid sequences for delivery to target cells. An AAV capsid is composed of 60 capsid protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397] or yet to be discovered, or a recombinant AAV based thereon, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

The minimal sequences required to package an expression cassette into an AAV viral particle are the AAV 5' and 3' ITRs, which may be of the same AAV origin as the capsid, or which are of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the MREG coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

The pharmaceutical compositions described herein are designed for delivery to subjects in need thereof by any suitable route or a combination of different routes. Direct delivery to the eye (optionally via ocular delivery, intraretinal injection, intravitreal, topical), or delivery via systemic routes, e.g., intraarterial, intraocular, intravenous, intramuscular, subcutaneous, intradermal, and other parental routes of administration. The proteins and/or vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus), alone or in combination with proteins.

Pharmaceutical Compositions and Administration

The compositions containing an MREG construct as described herein may be assessed for contamination by conventional methods and then formulated into a pharmaceutical composition intended for subretinal injection. Such formulation involves the use of a pharmaceutically and/or physiologically acceptable vehicle, excipient, or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween 20.

In certain embodiments of the methods of this invention, the pharmaceutical composition described above is administered to the subject by subretinal injection. The use of subretinal injection as the route of delivery is a critical component of this method, as intravitreal administration currently does not enable the same therapeutic effects.

Furthermore, in certain embodiments of the invention it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. These, and other desirable tests, are described in the examples below. In view of the imaging and functional studies, in some embodiments of the invention one or more injections are performed in the same eye in order to target different areas of retained photoreceptors. The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged photoreceptors is impacted. In another embodiment, the volume and/or concentration of the MREG composition is a greater amount, in order reach larger portions of the eye, including non-damaged photoreceptors.

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

An effective concentration of a recombinant adeno-associated virus carrying a nucleic acid sequence encoding the desired transgene under the control of the cell-specific promoter sequence desirably ranges between about $10^8$ and $10^{13}$ genomes copies per milliliter (gc/mL). Preferably, the concentration is from about $1.5 \times 10^9$ gc/mL to about $1.5 \times 10^{12}$ gc/mL, and more preferably from about $1.5 \times 10^9$ gc/mL to about $1.5 \times 10^{11}$ gc/mL. In one embodiment, the effective concentration is about $1.5 \times 10^{10}$ gc/mL. In another embodiment, the effective concentration is about $1.5 \times 10^{11}$ gc/mL. In another embodiment, the effective concentration is about $2.8 \times 10^{11}$ gc/mL. In yet another embodiment, the effective concentration is about $1.5 \times 10^{12}$ gc/mL. In another embodiment, the effective concentration is about $1.5 \times 10^{13}$ gc/mL. Alternatively, the rAAV are measured as described in S. K. McLaughlin et al, 1988 J. Virol., 62:1963. Suitable concentrations of viral vectors or genetic elements may be determined by one of skill in the art. Similarly, suitable concentrations for delivery of the MREG protein, e.g., about 0.001 mg to about 1000 mg, about 1 mg to about 500 mg, or higher or lower doses or concentrations may be selected.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the particular ocular disorder and the degree to which the disorder, if progressive, has developed.

A course of treatment may optionally involve repeat delivery of one or more MREG protein as described herein. Such treatment may involve protein-based therapies (including, e.g., delivery of a composition containing one or more MREG variants as described herein), administration of a single viral vector expressing at least one MREG (e.g., an AAV vector), or administration of different viral vector, or combinations of protein-based and/or vector-based therapies. Still other combinations may be selected using the viral vectors described herein. Optionally, the composition described herein may be combined in a regimen involving other drugs (e.g., anti-VEGF drugs), or protein-based therapies.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

The compositions described herein may be used in treating Stargardt's Disease by delivering the MREG to the subject, e.g., human patient. The compositions described herein may be used in treating macular degeneration by delivering the MREG to the subject, e.g., human patient.

In one aspect, the composition and method includes administering to the subject by subretinal injection an effective amount of a recombinant adeno-associated virus carrying a nucleic acid sequence encoding the MREG gene under the control of a promoter sequence which expresses the product of the gene in the ocular cells, specifically in the retinal pigment epithelial (RPE) cells of the subject. The method involves administering to the subject by subretinal injection an effective amount of a recombinant virus carrying a nucleic acid sequence encoding a normal retinal pigment epithelial (RPE) cell-specific gene under the control of a promoter sequence which expresses the product of the gene in RPE cells. Over-expression of the MREG gene provides to the cells an up-regulation of degradative capacity necessary to clear photoreceptor outer segment debris from the RPE.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Examples

Figure 1B:
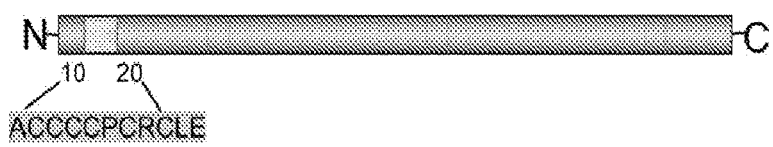
Figure 1C:
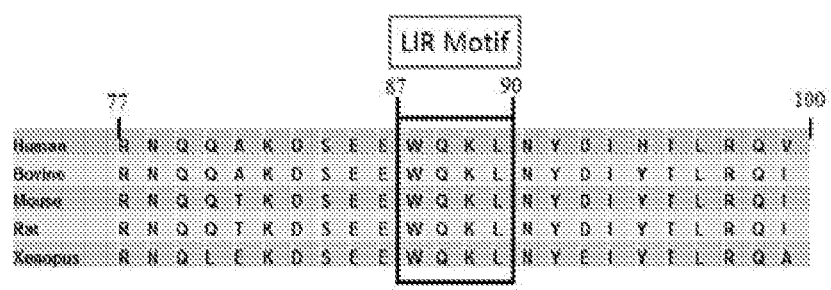
FIG. 1C provides an alignment of the LC3 interacting region (LIR) within MREG of human [SEQ ID NO:1], bovine [SEQ ID NO:2], mouse [SEQ ID NO: 3], rat [SEQ ID NO: 4], and xenopus [SEQ ID NO:5] marked by the box.

As described below, the accumulation of lipid-like auto fluorescent debris and the clearance of this toxic debris were studied using a hybrid autophagy-phagocytic pathway. Cells utilize numerous processes to identify and target ingested material for degradation these include phagocytosis and autophagy. A novel hybrid pathway that utilizes components of both of these pathways has been characterized and is termed LC3 associated phagocytosis (LAP). Using a combination of confocal imaging and biochemical techniques as well as in vitro and in vivo models this LAP process in the RPE's function as a professional phagocyte has been characterized. Moreover, a novel modulator of LAP, a small LC3 binding protein called melanoregulin, MREG, has been identified in these studies. MREG is a 28-32 Kda cargo sorting protein with a palmitoylation site on the N-terminus as well as an LC3 interacting region (LIR) within residues 10-20 illustrated in FIG. 1B and residues 87 to 90 illustrated in FIG. 1C. MREG appears to be required for complete degradation of ingested POS likely through the delivery of LC3 to the outer segment containing phagosome as depicted schematically in FIG. 1A. In view of this finding, a series of studies were designed to harness MREG as a mediator of LC3 dependent degradation of ingested components to alter RPE auto-fluorescence in a mouse model of Stargardt's disease. These further studies showed that over-expression of MREG in the RPE results in decreased lipofuscin-like toxic fluorescent debris, a hallmark of retinal degeneration in the ABCA4–/— model of human Stargardt's disease.

Studies were designed to determine if the accumulation of OS debris could be slowed down or prevented in a model of lipofuscin accumulation, the ABCA4–/– mouse RPE [Frost, L. S., Lopes, V., Bragin, A. Reyes-Reveles, J., Brancato, J., Mitchell, C. H., Williams, D. S. and Boesze-Battaglia, K. The Contribution of Melanoregulin to Microtubule-Associated Protein 1 Light Chain 3 (LC3) Associated Phagocytosis by the Retinal Pigment Epithelium. Molecular Neurobiology 2014. PMID:25301234.ONLINE Journal]. More particularly, the ABCA4–/– knockout mouse has delayed dark adaptation but normal final rod threshold relative to controls. At the histological level, degeneration of photoreceptors and the underlying retinal pigmented epithelium (RPE) occurs within and near the macula. The reason for the death of RPE cells, which are responsible for maintenance of photoreceptors and phagocytosis of their aging outer segments, is believed to be the accumulation of undigested lipid-like debris.

Figure 2:
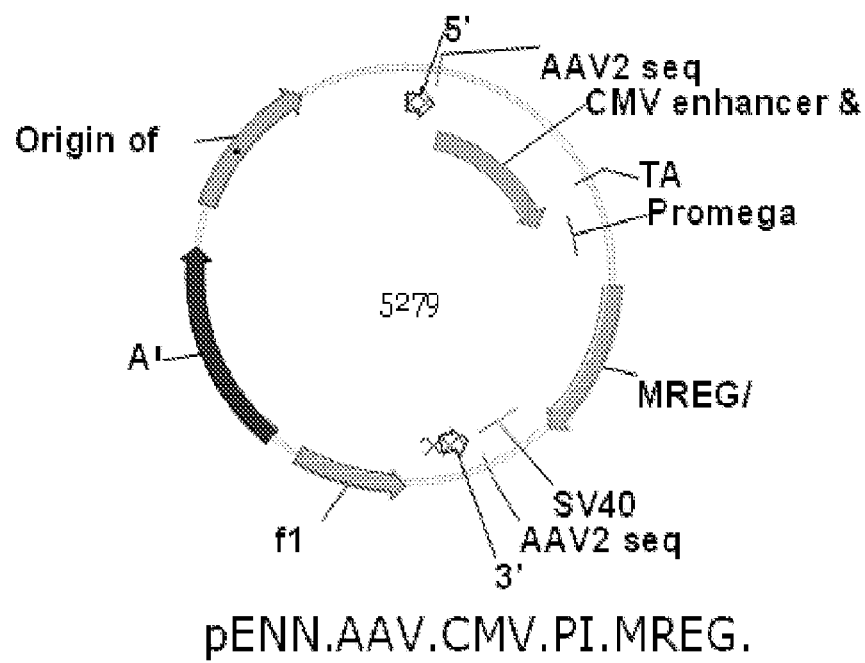
FIG. 2 is a schematic of pENN.AAV.CMV.PI.MREG.SV40 (p1690) vector map.

Recombinant AAV vector was based on pTR-UF2, a vector using the 472 bp mouse rod opsin promoter to drive expression of green fluorescent protein (GFP). To generate the recombinant vector, AAV-RPE65, the opsin promoter in pTR-UF2 was replaced with a CMV immediate early enhancer (381 bp)/chicken-actin (CA) promoter-exon 1-intron 1 (1352 bp) element followed by a poliovirus internal ribosome entry sequence (637 bp). The reporter/transgene GFP was upstream of the human MREG gene via flanking Not I sites and the orientation and reading frame confirmed by DNA sequence analysis. Plasmid DNA containing this construct was packaged into AAV particles employing iodixanol gradient purification followed by heparin-sepharose agarose column chromatography. The adenovirus associated vector was generated at the Penn Vector Core, Gene Therapy program and is designated pENN.AAV2/8.CMV.PI.MREG.SV40 (p1690), a vector map is shown as FIG. 2.

Using this vector, MREG was introduced into ABCA4–/– mice in an AAV vector, through sub-retinal injection and in vivo electroporation.

Figure 3A:
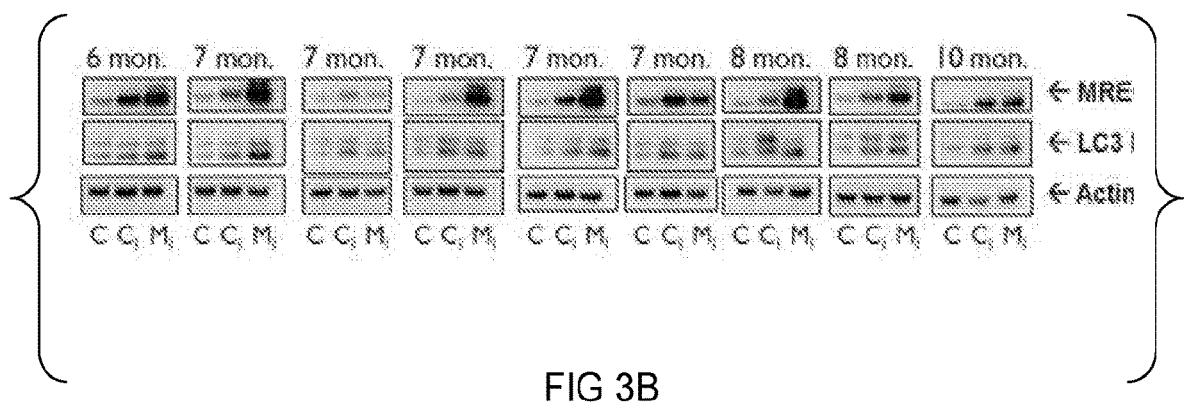
FIGS. 3A-3B provide quantitation of levels of MREG.
Figure 3B:
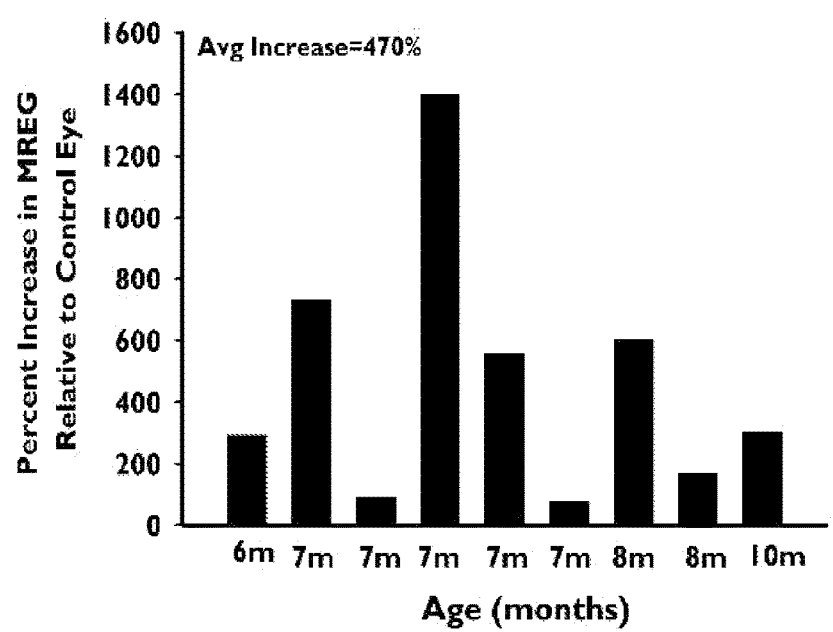
Figure 4A:
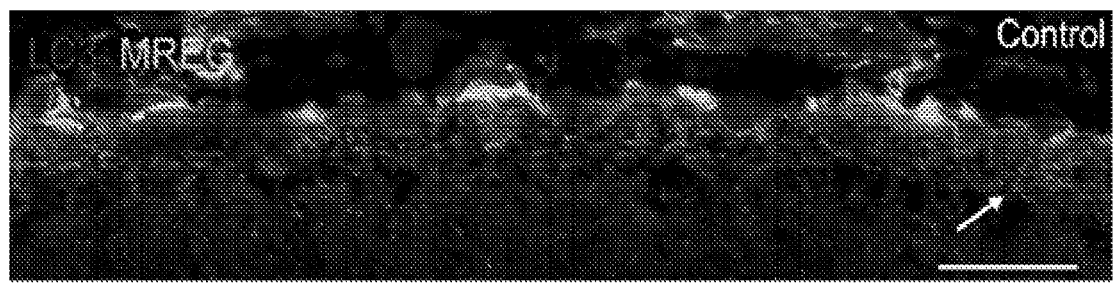
FIGS. 4A-4B provide two panels illustrating the results of MREG puncta increase in retinal pigment epithelial cells of ABCA4−/− mice injected with pENN.AAV.CMV.PI.MREG.SV40 (p1690). Eyecups prepared from ABCA4−/− mice (4 months old, 6 h after light onset) were fixed and stained with anti-MREG (mAb, Abnova) and anti-LC3 rabbit polyclonal (Cell Signaling). RPE=Retinal Pigment Epithelium. Scale bar=10 µm. Results are representative of two independent injections.
Figure 4B:
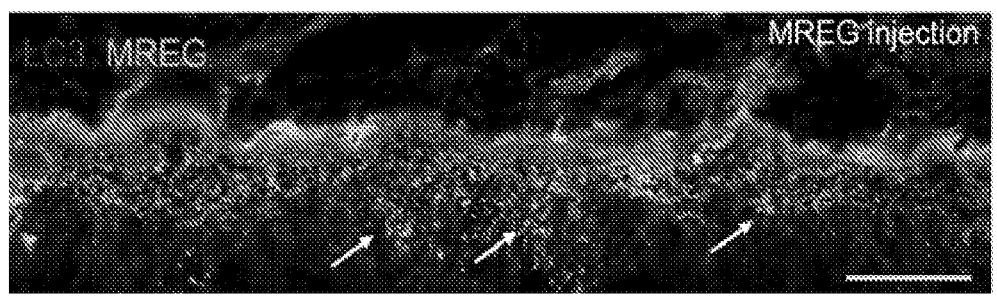

In brief, ABCA4–/– mice at post-natal day 2 (P2) were sedated and, 0.5 ul from m a $1.6 \times 10^{12}$ viral particle stock (Lot #1565), were sub-retinally injected and in vivo electroplated into the RPE with three, 50 second pulses, at 950 second intervals (100V). One eye was injected with the AAV vector the other was injected with vehicle control (no vector). Pups were returned to their cages and maintained in 12-hr daily light-dark cycle until analyzed. Mice were euthanized at various ages and RPE sections analyzed for fluorescent lipid conjugate using hyperspectral imaging and MREG and LC3 levels by conventional multi-fluor laser confocal imaging and quantitative Western blot. MREG levels increased up to 400% in mice injected with the AAV vector compared to vehicle controls (shown in FIGS. 3 A and B). MREG expression levels were found to be stable over a ten month period and levels of the MREG binding partner LC3 were unaffected suggesting no off target effects. As shown in FIG. 4, MREG puncta in the experimental group was increased (as indicated by white arrows) in the ABCA4-/- mouse RPE compared to controls.

Figure 5A:
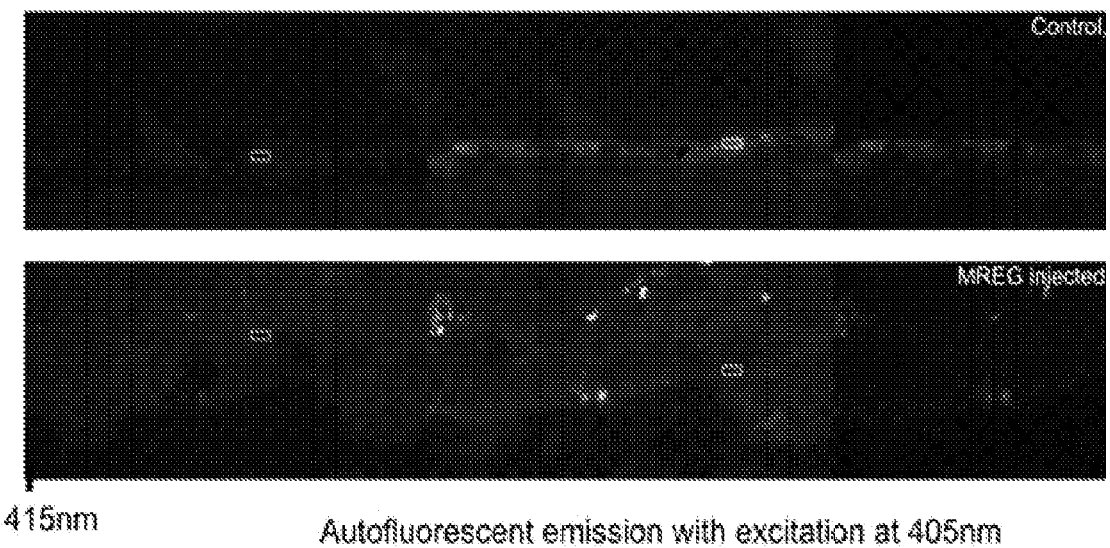
FIG. 5A is two panels showing hyper-spectral imaging of RPE from ABCA4−/− mice injected with pENN.AAV.CMV.PI.MREG.SV40, labeled HMREG2 (Panel A) compared to vehicle controls (Panel B). Eye cups prepared from ABCA4−/− mice (10 months old, 6 h after light onset) were analyzed for spectral profiles RPE=Retinal Pigment Epithelium. Scale bar=5 µm.
Figure 5B:
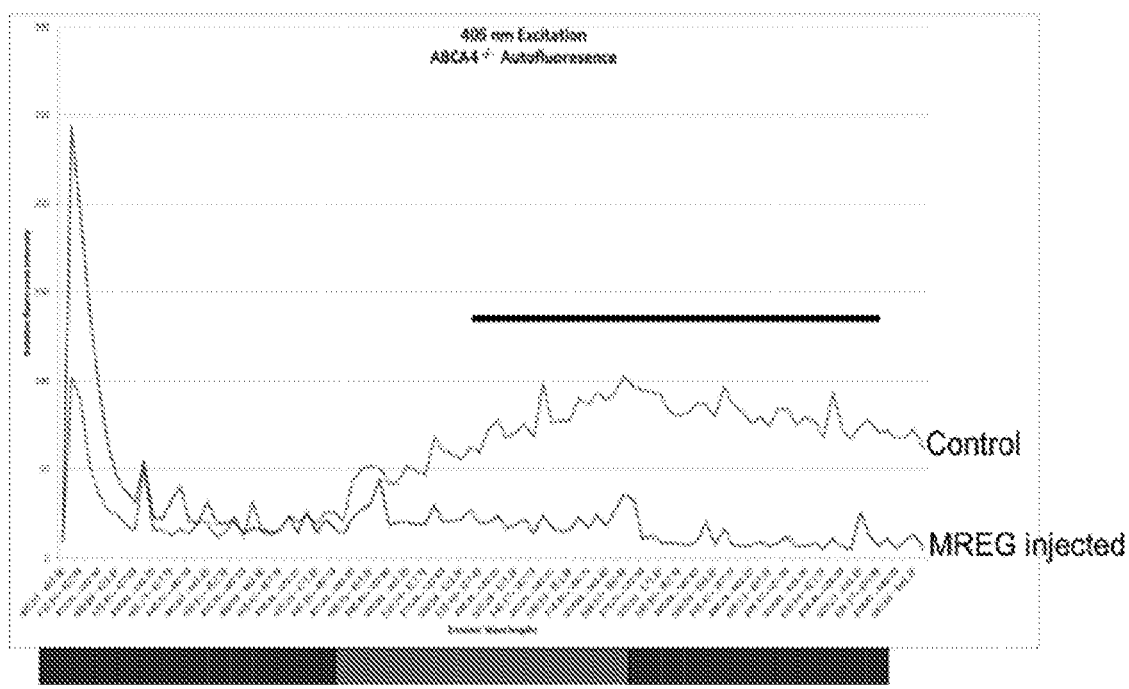
FIG. 5C is a spectral analysis of auto-fluorescent components. Hyper-spectral imaging of RPE from ABCA4−/− mice injected with pENN.AAV.CMV.PI.MREG.SV40 compared to vehicle control. Regions indicted in FIG. 5A as squares were analyzed in detail across the entire emission spectra (with excitation at 405 m). Based on previously published studies the majority of the toxic fluorescent debris is between 520 nm and 620 nm. These regions are indicted with a black bar on the graph. Eyecups prepared from aged ABCA4−/− mice (10 months old, 6 h after light onset) were analyzed for spectral profiles. RPE=Retinal Pigment Epithelium. Scale bar=10 μm.
Figure 6A:
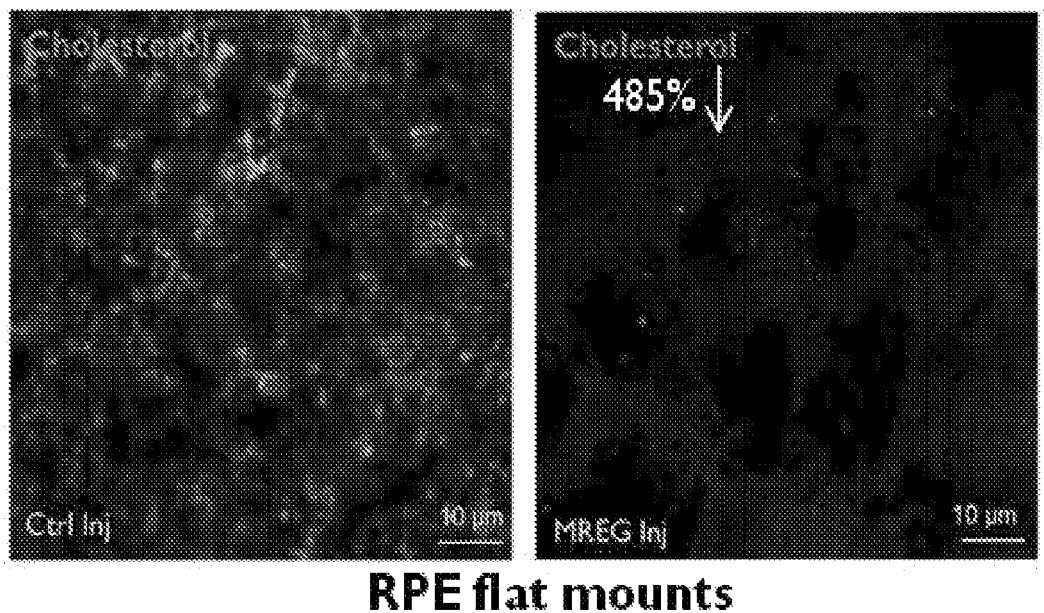
Figure 6B:
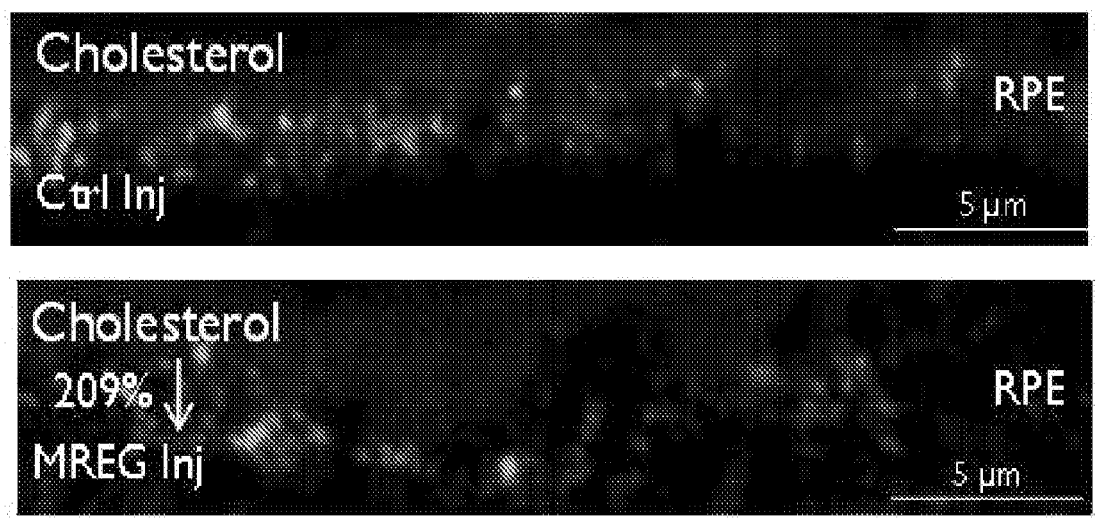
Figure 7C:
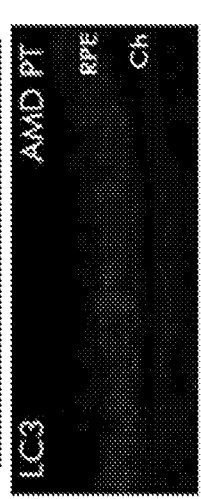
FIGS. 7A-7D provide an analysis of human retinal sections for MREG and LC3 levels between age-matched normal (no-disease) donor (FIGS. 7A-7B) and AMD patients (FIGS. 7C-7D). Other properties of these patients have been characterized in (Dunaief, Dentchev et al. Arch Opththalmol. 2002 November; 120(11):1435-42).
Figure 7D:
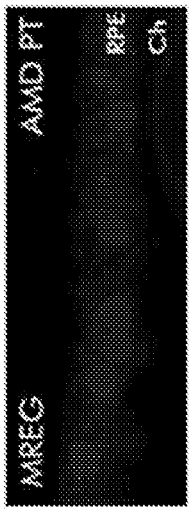
Figure 7A:
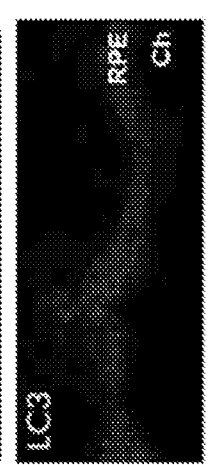
Figure 7B:
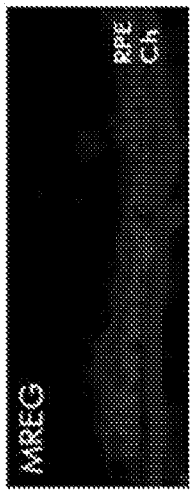
Figure 8A:
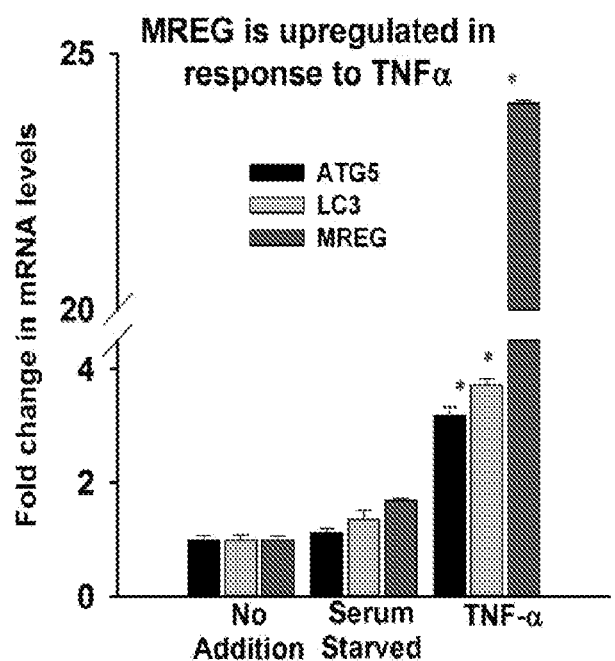
FIG. 8A shows results from a study, in which, in brief, human ARPE-19 cells at 80-85% confluence (72-h growth in DMEM/F12+10% FBS at 37° C.) were serum-starved for 8 h and treated with TNF-α (Sigma-Aldrich, St. Louis, Mo.) (10 ng/ml) and $H_2O_2$ to induce oxidative stress cell were analyzed for mRNA levels of Mreg, Atg5 and LC3, determined by qPCR after 12 hrs of treatment. Results shown are an average of 3 independent experiments each analyzed in duplicate for and n=6, p<0.005.
Figure 8B:
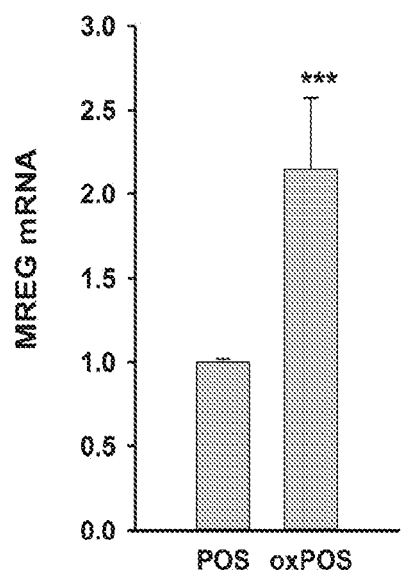
FIG. 8B shows MREG mRNA levels determined upon the addition of endogenous substrates photoreceptor outer segments (POS) and oxidized POS, generated to mimic intracellular RPE debris mRNA levels of Mreg, were determined by qPCR after 3 hrs of POS or OxPOS incubation. Results shown are an average of 3 independent experiments each analyzed in duplicate for and n=6, p<0.005.

Further detailed analysis using hyper-spectral imaging, a technique that detects various classes of toxic fluorescent debris based on the wavelength of fluorescence emission was utilized to test the effectiveness of enhanced MREG expression. ABCA4-/- mouse RPE accumulate auto-fluorescent debris over time as degradation processes are compromised. Our hypothesis predicted that if MREG acts as a mediator of debris degradation, then in the experimental eye the extent of auto-fluorescence associated with lipofuscin-like components should decrease. As shown in FIG. 5A, the extent of auto-fluorescence in MREG AAV expressing ABCA4-/- mouse RPE is less than that observed in the control RPE (Panel A versus Panel B, respectively. When the auto-fluorescence emission (at $\lambda_{ex}=405$) corresponding to lipofuscin like components in the 520 nm to 620 nm range was compared (FIGS. 5A-5B), there was a 3-fold decrease in auto-fluorescence in the presence of excess MREG. Disease is characterized by intracellular accumulation of cholesterol debris, as shown in FIG. 6, upregulation of MREG expression decreased intracellular cholesterol levels by 209%-485%.

Sequence Listing Free Text

The following information is provided for sequences containing free text under numeric identifier <223>.

| SEQ ID NO: (containing free text) | Free text under <223> |
|---|---|
| 1 | <223> aa 77-100 with LIR motif (87-90) |
| 2 | <223> bovine mutant MREG-W87A and MREGL90A |
| 3 | <223> mutant MREG-W87A and MREG L90A |
| 4 | <223> rat mutant MREG-W87A and MREG L90A |
| 5 | <223> xenopus mutant-MREG-W87A and MREG L90A |
| 6 | <223> DS MREG delta 10 |
| 7 | <223> Synthetic Construct |
| 8 | <223> Synthetic Construct |
| 9 | <223> DS MREG Delta 30 |
| 10 | <223> Synthetic Construct |
| 11 | <223> Synthetic Construct |
| 12 | <223> Synthetic Construct |
| 13 | <223> USMREGDelta10 |
| 14 | <223> Synthetic Construct |
| 15 | <223> Synthetic Construct |
| 16 | <223> Synthetic Construct |
| 17 | <223> Synthetic Construct |
| 18 | <223> Synthetic Construct |
| 19 | <223> Synthetic Construct |
| 20 | <223> Synthetic Construct |
| 21 | <223> Synthetic Construct |
| 22 | <223> Synthetic Construct |
| 23 | <223> Synthetic Construct |
| 24 | <223> Synthetic Construct |
| 25 | <223> Synthetic Construct |
| 26 | <223> Synthetic Construct |
| 27 | <223> DS MREGDeleta30, Clone #1 |
| 28 | <223> Synthetic Construct |
| 29 | <223> Synthetic Construct |
| 30 | <223> Synthetic Construct |
| 31 | <223> USMREGDelta20, Clone #1 |
| 32 | <223> Synthetic Construct |
| 33 | <223> Synthetic Construct |
| 34 | <223> Synthetic Construct |
| 35 | <223> USMREGDelta30, clone #1 |
| 36 | <223> Synthetic Construct |
| 37 | <223> DS MREG forward primer |
| 38 | <223> DSMREGDelta 10 reverse primer |
| 39 | <223> US MREG forward primer |
| 40 | <223> US MREG reverse primer |
| 41 | <223> Mus musculus (N-terminal GFP) forward primer |
| 42 | <223> Mus musculus N-terminal GFP reverse primer |
| 43 | <223> C-terminal GFP reverse primer |
| 44 | <223> L90A mutation on mMREG |
| 45 | <223> Synthetic Construct |
| 46 | <223> Mus musculus GFP-MREG (W87A) forward primer |
| 47 | <223> GFP-MREG (W87A) Clone #1010 Primers (N-terminal GFP): |
| 48 | <223> GFP-MREG C-terminal GFP reverse primer |
| 49 | <223> W87A mutation on mMREG |
| 50 | <223> Synthetic Construct |
| 51 | <223> DS MREGdelta20 9pGEXhMREGdelta20, clone #6) |
| 52 | <223> Synthetic Construct |
| 53 | <223> Synthetic Construct |
| 54 | <223> Synthetic Construct |
| 57 | <223> Engineered mutant MREG protein US Delta 10 |
| 58 | <223> Engineered mutant MREG US Delta 20 |
| 59 | <223> Engineered mutant MREG US Delta 30 |
| 60 | <223> Engineered mutant MREG DS Delta 10 |
| 61 | <223> Engineered mutant MREG DS Delta 20 |
| 62 | <223> Engineered mutant MREG DS Delta 30 |

All publications and patent applications cited in this specification are incorporated herein by reference. U.S. Provisional Application No. 62/239,480, filed Oct. 9, 2015, is hereby incorporated by reference in its entirety, as is the appended Sequence Listing. While the invention has been described with reference to particular embodiments, it will be appreciated that modifications can be made without departing from the spirit of the invention. Such modifications are intended to fall within the scope of the appended claims.

SEQUENCE LISTING

<160> NUMBER OF SEQ ID NOS: 62

<210> SEQ ID NO 1
<211> LENGTH: 24
<212> TYPE: PRT
<213> ORGANISM: Artificial Sequence
<220> FEATURE:
<223> OTHER INFORMATION: aa 77-100 with LIR motif (87-90)

<400> SEQUENCE: 1

Arg Asn Gln Gln Ala Lys Asp Ser Glu Glu Trp Gln Lys Leu Asn Tyr
1               5                   10                  15

Asp Ile His Thr Leu Arg Gln Val
            20

<210> SEQ ID NO 2
<211> LENGTH: 24
<212> TYPE: PRT
<213> ORGANISM: Artificial Sequence
<220> FEATURE:
<223> OTHER INFORMATION: bovine mutant MREG-W87A and MREGL90A

<400> SEQUENCE: 2

Arg Asn Gln Gln Ala Lys Asp Ser Glu Glu Trp Gln Lys Leu Asn Tyr
1               5                   10                  15

Asp Ile Tyr Thr Leu Arg Gln Ile
            20

<210> SEQ ID NO 3
<211> LENGTH: 24
<212> TYPE: PRT
<213> ORGANISM: Artificial sequence
<220> FEATURE:
<223> OTHER INFORMATION: mutant MREG-W87A and MREG L90A

<400> SEQUENCE: 3

Arg Asn Gln Gln Thr Lys Asp Ser Glu Glu Trp Gln Lys Leu Asn Tyr
1               5                   10                  15

Asp Ile Tyr Thr Leu Arg Gln Ile
            20

<210> SEQ ID NO 4
<211> LENGTH: 24
<212> TYPE: PRT
<213> ORGANISM: Artificial sequence
<220> FEATURE:
<223> OTHER INFORMATION: rat mutant MREG-W87A and MREG L90A

<400> SEQUENCE: 4

Arg Asn Gln Gln Thr Lys Asp Ser Glu Glu Trp Gln Lys Leu Asn Tyr
1               5                   10                  15

Asp Ile Tyr Thr Leu Arg Gln Ile
            20

<210> SEQ ID NO 5
<211> LENGTH: 24
<212> TYPE: PRT
<213> ORGANISM: Artificial sequence
<220> FEATURE:
<223> OTHER INFORMATION: xenopus mutant-MREG-W87A and MREG L90A

<400> SEQUENCE: 5

Arg Asn Gln Leu Glu Lys Asp Ser Glu Glu Trp Gln Lys Leu Asn Tyr
1               5                   10                  15

```
Glu Ile Tyr Thr Leu Arg Gln Ala
             20

<210> SEQ ID NO 6
<211> LENGTH: 911
<212> TYPE: DNA
<213> ORGANISM: Artificial Sequence
<220> FEATURE:
<223> OTHER INFORMATION: DS MREG delta 10
<220> FEATURE:
<221> NAME/KEY: CDS
<222> LOCATION: (62)..(703)

<400> SEQUENCE: 6
tcatctcaat cggatctggt tcgcgtggat ccccggggct gagggactgg aaacagtatt        60 c atg ggg ctg agg gac tgg ctg aga acc gtg tgc tgc tgc tgc ggg tgc      109
  Met Gly Leu Arg Asp Trp Leu Arg Thr Val Cys Cys Cys Cys Gly Cys
  1               5                   10                  15 gag tgc ttg gag gag cgc gcc ctg cct gag aag gag ccc ctc gtc agt        157
Glu Cys Leu Glu Glu Arg Ala Leu Pro Glu Lys Glu Pro Leu Val Ser
             20                  25                  30 gat aac aat cca tat tcc tca ttt gga gca act ctg gtg agg gat gat        205
Asp Asn Asn Pro Tyr Ser Ser Phe Gly Ala Thr Leu Val Arg Asp Asp
         35                  40                  45 gag aag aat tta tgg agt atg ccc cat gat gtg tcc cac aca gag gca        253
Glu Lys Asn Leu Trp Ser Met Pro His Asp Val Ser His Thr Glu Ala
50                  55                  60 gac gac gac aga acc ctg tac aat ttg ata gtc att cgt aat cag cag        301
Asp Asp Asp Arg Thr Leu Tyr Asn Leu Ile Val Ile Arg Asn Gln Gln
65                  70                  75                  80 gcc aaa gac tca gag gag tgg cag aag ctc aac cat gat atc cat acc        349
Ala Lys Asp Ser Glu Glu Trp Gln Lys Leu Asn His Asp Ile His Thr
                 85                  90                  95 ctg cgg cag gtt cga agg gaa gta aga aac aga tgg aag tgc atc tta        397
Leu Arg Gln Val Arg Arg Glu Val Arg Asn Arg Trp Lys Cys Ile Leu
            100                 105                 110 gaa gat tta ggt ttt caa aag gaa gct gac tct ttg ttg tca gtg act        445
Glu Asp Leu Gly Phe Gln Lys Glu Ala Asp Ser Leu Leu Ser Val Thr
        115                 120                 125 aaa ctc agc acc atc agt gat tct aaa aac aca agg aaa gct cga gag        493
Lys Leu Ser Thr Ile Ser Asp Ser Lys Asn Thr Arg Lys Ala Arg Glu
    130                 135                 140 atg ttg tta aaa ctg gct gaa gaa acc aat att ttc cca aca agt tgg        541
Met Leu Leu Lys Leu Ala Glu Glu Thr Asn Ile Phe Pro Thr Ser Trp
145                 150                 155                 160 gag ctc tca gag aga tat ctc ttt gtt gtg gac cgt ctc att gca ctt        589
Glu Leu Ser Glu Arg Tyr Leu Phe Val Val Asp Arg Leu Ile Ala Leu
                165                 170                 175 gat gct gca gag gag ttc ttt aag ctt gct cgt cga act tac ccc aag        637
Asp Ala Ala Glu Glu Phe Phe Lys Leu Ala Arg Arg Thr Tyr Pro Lys
            180                 185                 190 aag cct ggg gtt cca tgc ctg gca gat ggc cag aaa taa ctg cac tac        685
Lys Pro Gly Val Pro Cys Leu Ala Asp Gly Gln Lys     Leu His Tyr
        195                 200                 205 ctt ccg ttt cca agt ccc gggaattcat cgtgactgac tgacgatctg               733
Leu Pro Phe Pro Ser Pro
            210 cctcgcgcgt ttcggtgatg acggtgaaaa cctctgacac atgcagctcc cggagacggt       793 cacagcttgt ctgtaagcgg atgccgggag cagacagccc gtcaggcgcg tcagcggtgt       853 tggcggtgtc ggggcgcagc catgacccag tcacgtagcg awtagcggag tgtataaa        911
```

<210> SEQ ID NO 7
<211> LENGTH: 204
<212> TYPE: PRT
<213> ORGANISM: Artificial Sequence
<220> FEATURE:
<223> OTHER INFORMATION: Synthetic Construct

<400> SEQUENCE: 7

```
Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
            20                  25                  30

Asp Asn Asn Pro Tyr Ser Ser Phe Gly Ala Thr Leu Val Arg Asp Asp
        35                  40                  45

Glu Lys Asn Leu Trp Ser Met Pro His Asp Val Ser His Thr Glu Ala
    50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn His Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
    130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys Leu Ala Arg Arg Thr Tyr Pro Lys
            180                 185                 190

Lys Pro Gly Val Pro Cys Leu Ala Asp Gly Gln Lys
        195                 200
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

```
Leu His Tyr Leu Pro Phe Pro Ser Pro
1               5
```

<210> SEQ ID NO 9
<211> LENGTH: 931
<212> TYPE: DNA
<213> ORGANISM: Artificial sequence
<220> FEATURE:
<223> OTHER INFORMATION: DS MREG Delta 30
<220> FEATURE:
<221> NAME/KEY: CDS
<222> LOCATION: (67)..(708)

<400> SEQUENCE: 9

```
gyccaatctc aaatcggatc tggttccgcg tggatccccg gggctgaggg actggaaaca      60 gtattc atg ggg ctg agg gac tgg ctg aga acc gtg tgc tgc tgc tgc        108
```

```
         Met Gly Leu Arg Asp Trp Leu Arg Thr Val Cys Cys Cys Cys
         1               5                   10 ggg tgc gag tgc ttg gag gag cgc gcc ctg cct gag aag gag ccc ctc       156
Gly Cys Glu Cys Leu Glu Glu Arg Ala Leu Pro Glu Lys Glu Pro Leu
15                  20                  25                  30 gtc agt gat aac aat cca tat tcc tca ttt gga gca act ctg gtg agg       204
Val Ser Asp Asn Asn Pro Tyr Ser Ser Phe Gly Ala Thr Leu Val Arg
                35                  40                  45 gat gat gag aag aat tta tgg agt atg ccc cat gat gtg tcc cac aca       252
Asp Asp Glu Lys Asn Leu Trp Ser Met Pro His Asp Val Ser His Thr
            50                  55                  60 gag gca gac gac gac aga acc ctg tac aat ttg ata gtc att cgt aat       300
Glu Ala Asp Asp Asp Arg Thr Leu Tyr Asn Leu Ile Val Ile Arg Asn
65                  70                  75 cag cag gcc aaa gac tca gag gag tgg cag aag ctc aac cat gat atc       348
Gln Gln Ala Lys Asp Ser Glu Glu Trp Gln Lys Leu Asn His Asp Ile
        80                  85                  90 cat acc ctg cgg cag gtt cga agg gaa gta aga aac aga tgg aag tgc       396
His Thr Leu Arg Gln Val Arg Arg Glu Val Arg Asn Arg Trp Lys Cys
95                  100                 105                 110 atc tta gaa gat tta ggt ttt caa aag gaa gct gac tct ttg tca           444
Ile Leu Glu Asp Leu Gly Phe Gln Lys Glu Ala Asp Ser Leu Leu Ser
                115                 120                 125 gtg act aaa ctc agc acc atc agt gat tct aaa aac aca agg aaa gct       492
Val Thr Lys Leu Ser Thr Ile Ser Asp Ser Lys Asn Thr Arg Lys Ala
            130                 135                 140 cga gag atg ttg tta aaa ctg gct gaa gaa acc aat att ttc cca aca       540
Arg Glu Met Leu Leu Lys Leu Ala Glu Glu Thr Asn Ile Phe Pro Thr
        145                 150                 155 agt tgg gag ctc tca gag aga tat ctc ttt gtt gtg gac cgt ctc att      588
Ser Trp Glu Leu Ser Glu Arg Tyr Leu Phe Val Val Asp Arg Leu Ile
160                 165                 170 gca ctt gat gct gca gaa gag ttc ttt aag taa gct cgt cga act tac      636
Ala Leu Asp Ala Ala Glu Glu Phe Phe Lys     Ala Arg Arg Thr Tyr
175                 180                     185 ccc aag aag cct ggg gtt cca tgc ctg gca gat ggc cag aaa taa ctg      684
Pro Lys Lys Pro Gly Val Pro Cys Leu Ala Asp Gly Gln Lys     Leu
190                 195                 200 cac tac ctt ccg ttt cca agt ccc gggaattcat cgtgactgac tgacgatctg     738
His Tyr Leu Pro Phe Pro Ser Pro
205                 210 cctcgcgcgt ttcggtgatg acggtgaaaa cctctgacac atgcagctcc cggagacggt    798
cacagcttgt ctgtaagcgg atgccgggag cagacaagcc cgtcaggcgc gtcagcgggt    858
gttggcgggt gtcgggcgc agccatgacc cagtcacgta gcgatagcgg agtgtataaa    918
ttcttgaagr acg                                                        931

<210> SEQ ID NO 10
<211> LENGTH: 184
<212> TYPE: PRT
<213> ORGANISM: Artificial sequence
<220> FEATURE:
<223> OTHER INFORMATION: Synthetic Construct

<400> SEQUENCE: 10

Met Gly Leu Arg Asp Trp Leu Arg Thr Val Cys Cys Cys Cys Gly Cys
1               5                   10                  15

Glu Cys Leu Glu Glu Arg Ala Leu Pro Glu Lys Glu Pro Leu Val Ser
            20                  25                  30
```

```
Asp Asn Asn Pro Tyr Ser Ser Phe Gly Ala Thr Leu Val Arg Asp Asp
            35                  40                  45

Glu Lys Asn Leu Trp Ser Met Pro His Asp Val Ser His Thr Glu Ala
 50                  55                  60

Asp Asp Asp Arg Thr Leu Tyr Asn Leu Ile Val Ile Arg Asn Gln Gln
 65                  70                  75                  80

Ala Lys Asp Ser Glu Glu Trp Gln Lys Leu Asn His Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
            115                 120                 125

Lys Leu Ser Thr Ile Ser Asp Ser Lys Asn Thr Arg Lys Ala Arg Glu
            130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys
            180

<210> SEQ ID NO 11
<211> LENGTH: 19
<212> TYPE: PRT
<213> ORGANISM: Artificial sequence
<220> FEATURE:
<223> OTHER INFORMATION: Synthetic Construct

<400> SEQUENCE: 11

Ala Arg Arg Thr Tyr Pro Lys Lys Pro Gly Val Pro Cys Leu Ala Asp
1               5                   10                  15

Gly Gln Lys

<210> SEQ ID NO 12
<211> LENGTH: 9
<212> TYPE: PRT
<213> ORGANISM: Artificial sequence
<220> FEATURE:
<223> OTHER INFORMATION: Synthetic Construct

<400> SEQUENCE: 12

Leu His Tyr Leu Pro Phe Pro Ser Pro
1               5

<210> SEQ ID NO 13
<211> LENGTH: 940
<212> TYPE: DNA
<213> ORGANISM: Artificial Sequence
<220> FEATURE:
<223> OTHER INFORMATION: USMREGDelta10
<220> FEATURE:
<221> NAME/KEY: CDS
<222> LOCATION: (275)..(940)

<400> SEQUENCE: 13
actgcacggt gcaccaatgc ttctggcgtc aggcagccat cgaagctgtg gtatgctgtg      60
caggtcgtaa atcactgcat aattcgtgtc gctcaaggcg cactcccgtt ctggataatg     120
ttttttgcgc cgacatcata acggttctgg caaatattct gaaatgagct gttgacaatt     180
aatcatcggc tcgtataatg tgtggaattg tgagcggata acaatttcac acaggaaaca     240
```

-continued

```
gtattcatgg ggctgaggga ctggaaacag tatt cat ggg gct gag gga ctg gct   295
                                    His Gly Ala Glu Gly Leu Ala
                                      1               5 gag aac cgt gtg ctg ctg ctg cgg gtg cga gtg ctt gga gga gcg cgc   343
Glu Asn Arg Val Leu Leu Leu Arg Val Arg Val Leu Gly Gly Ala Arg
         10                  15                  20 cct gcc tga gaa gga gcc cct cgt cag tga taa caa tcc ata ttc ctc   391
Pro Ala     Glu Gly Ala Pro Arg Gln         Gln Ser Ile Phe Leu
     25                  30                              35 att tgg agc aac tct ggt gag gga tga tga gaa gaa ttt atg gag tat   439
Ile Trp Ser Asn Ser Gly Glu Gly             Glu Glu Phe Met Glu Tyr
             40                  45                              50 gcc cca tga tgt gtc cca cac aga ggc aga cga cag aac cct gta       487
Ala Pro     Cys Val Pro His Arg Gly Arg Arg Gln Asn Pro Val
                     55                  60                  65 caa ttt gat agt cat tcg taa tca gca ggc caa aga ctc aga gga gtg   535
Gln Phe Asp Ser His Ser     Ser Ala Gly Gln Arg Leu Arg Gly Val
             70                  75                              80 gca gaa gct caa cta tga tat cca tac cct gcg gca ggt tcg aag gga   583
Ala Glu Ala Gln Leu     Tyr Pro Tyr Pro Ala Ala Gly Ser Lys Gly
             85                      90                          95 agt aag aaa cag atg gaa gtg cat ctt aga aga ttt agg ttt tca aaa   631
Ser Lys Lys Gln Met Glu Val His Leu Arg Arg Phe Arg Phe Ser Lys
                100                 105                 110 gga agc tga ctc ttt gtt gtc agt gac taa act cag cac cat cag tga   679
Gly Ser     Leu Phe Val Val Ser Asp     Thr Gln His His Gln
                    115                 120 ttc taa aaa cac aag gaa agc tcg aga gat gtt gtt aaa act ggc tga   727
Phe     Lys His Lys Glu Ser Ser Arg Asp Val Val Lys Thr Gly
125             130                 135 aga aac caa tat ttt ccc aac aag ttg gga gct ctc aga gag ata tct   775
Arg Asn Gln Tyr Phe Pro Asn Lys Leu Gly Ala Leu Arg Glu Ile Ser
        140                 145                 150 ctt tgt tgt gga ccg tct cat tgc act tga tgc tgc aga gga gtt ctt   823
Leu Cys Cys Gly Pro Ser His Cys Thr     Cys Cys Arg Gly Val Leu
155                 160                     165 taa gct tgc tcg tcg aac tta ccc caa gaa gcc tgg ggt tcc atg cct   871
    Ala Cys Ser Ser Asn Leu Pro Gln Glu Ala Trp Gly Ser Met Pro
    170                 175                 180 ggc aga tgg cca gac cat ggc ccc tat act agg tta ttg gaa aat aag   919
Gly Arg Trp Pro Asp His Gly Pro Tyr Thr Arg Leu Leu Glu Asn Lys
185                 190                 195                 200 ggc ctg tgc aac cca ctc gat                                       940
Gly Leu Cys Asn Pro Leu Asp
                205
```

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

His Gly Ala Glu Gly Leu Ala Glu Asn Arg Val Leu Leu Leu Arg Val
1               5                   10                  15

Arg Val Leu Gly Gly Ala Arg Pro Ala
            20                  25

<210> SEQ ID NO 15
<211> LENGTH: 6

```
<212> TYPE: PRT
<213> ORGANISM: Artificial Sequence
<220> FEATURE:
<223> OTHER INFORMATION: Synthetic Construct

<400> SEQUENCE: 15

Glu Gly Ala Pro Arg Gln
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Gln Ser Ile Phe Leu Ile Trp Ser Asn Ser Gly Glu Gly
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Glu Glu Phe Met Glu Tyr Ala Pro
1               5

<210> SEQ ID NO 18
<211> LENGTH: 19
<212> TYPE: PRT
<213> ORGANISM: Artificial Sequence
<220> FEATURE:
<223> OTHER INFORMATION: Synthetic Construct

<400> SEQUENCE: 18

Cys Val Pro His Arg Gly Arg Arg Gln Asn Pro Val Gln Phe Asp
1               5                   10                  15

Ser His Ser

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Ser Ala Gly Gln Arg Leu Arg Gly Val Ala Glu Ala Gln Leu
1               5                   10

<210> SEQ ID NO 20
<211> LENGTH: 28
<212> TYPE: PRT
<213> ORGANISM: Artificial Sequence
<220> FEATURE:
<223> OTHER INFORMATION: Synthetic Construct

<400> SEQUENCE: 20

Tyr Pro Tyr Pro Ala Ala Gly Ser Lys Gly Ser Lys Lys Gln Met Glu
1               5                   10                  15

Val His Leu Arg Arg Phe Arg Phe Ser Lys Gly Ser
            20                  25
```

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Leu Phe Val Val Ser Asp
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Thr Gln His His Gln
1               5

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

Lys His Lys Glu Ser Ser Arg Asp Val Val Lys Thr Gly
1               5                   10

<210> SEQ ID NO 24
<211> LENGTH: 25
<212> TYPE: PRT
<213> ORGANISM: Artificial Sequence
<220> FEATURE:
<223> OTHER INFORMATION: Synthetic Construct

<400> SEQUENCE: 24

Arg Asn Gln Tyr Phe Pro Asn Lys Leu Gly Ala Leu Arg Glu Ile Ser
1               5                   10                  15

Leu Cys Cys Gly Pro Ser His Cys Thr
            20                  25

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Cys Cys Arg Gly Val Leu
1               5

<210> SEQ ID NO 26
<211> LENGTH: 38
<212> TYPE: PRT
<213> ORGANISM: Artificial Sequence
<220> FEATURE:
<223> OTHER INFORMATION: Synthetic Construct

<400> SEQUENCE: 26

```
Ala Cys Ser Ser Asn Leu Pro Gln Glu Ala Trp Gly Ser Met Pro Gly
1               5                   10                  15

Arg Trp Pro Asp His Gly Pro Tyr Thr Arg Leu Leu Glu Asn Lys Gly
            20                  25                  30

Leu Cys Asn Pro Leu Asp
            35

<210> SEQ ID NO 27
<211> LENGTH: 931
<212> TYPE: DNA
<213> ORGANISM: Artificial sequence
<220> FEATURE:
<223> OTHER INFORMATION: DS MREGDelata30, Clone #1
<220> FEATURE:
<221> NAME/KEY: CDS
<222> LOCATION: (67)..(708)

<400> SEQUENCE: 27
gyccaatctc aaatcggatc tggttccgcg tggatccccg gggctgaggg actggaaaca      60 gtattc atg ggg ctg agg gac tgg ctg aga acc gtg tgc tgc tgc tgc       108
       Met Gly Leu Arg Asp Trp Leu Arg Thr Val Cys Cys Cys Cys
       1               5                   10 ggg tgc gag tgc ttg gag gag cgc gcc ctg cct gag aag gag ccc ctc      156
Gly Cys Glu Cys Leu Glu Glu Arg Ala Leu Pro Glu Lys Glu Pro Leu
15                  20                  25                  30 gtc agt gat aac aat cca tat tcc tca ttt gga gca act ctg gtg agg      204
Val Ser Asp Asn Asn Pro Tyr Ser Ser Phe Gly Ala Thr Leu Val Arg
                35                  40                  45 gat gat gag aag aat tta tgg agt atg ccc cat gat gtg tcc cac aca      252
Asp Asp Glu Lys Asn Leu Trp Ser Met Pro His Asp Val Ser His Thr
            50                  55                  60 gag gca gac gac gac aga acc ctg tac aat ttg ata gtc att cgt aat      300
Glu Ala Asp Asp Asp Arg Thr Leu Tyr Asn Leu Ile Val Ile Arg Asn
        65                  70                  75 cag cag gcc aaa gac tca gag gag tgg cag aag ctc aac cat gat atc      348
Gln Gln Ala Lys Asp Ser Glu Glu Trp Gln Lys Leu Asn His Asp Ile
    80                  85                  90 cat acc ctg cgg cag gtt cga agg gaa gta aga aac aga tgg aag tgc      396
His Thr Leu Arg Gln Val Arg Arg Glu Val Arg Asn Arg Trp Lys Cys
95                  100                 105                 110 atc tta gaa gat tta ggt ttt caa aag gaa gct gac tct ttg tca          444
Ile Leu Glu Asp Leu Gly Phe Gln Lys Glu Ala Asp Ser Leu Leu Ser
                115                 120                 125 gtg act aaa ctc agc acc atc agt gat tct aaa aac aca agg aaa gct      492
Val Thr Lys Leu Ser Thr Ile Ser Asp Ser Lys Asn Thr Arg Lys Ala
            130                 135                 140 cga gag atg ttg tta aaa ctg gct gaa gaa acc aat att ttc cca aca      540
Arg Glu Met Leu Leu Lys Leu Ala Glu Glu Thr Asn Ile Phe Pro Thr
        145                 150                 155 agt tgg gag ctc tca gag aga tat ctc ttt gtt gtg gac cgt ctc att      588
Ser Trp Glu Leu Ser Glu Arg Tyr Leu Phe Val Val Asp Arg Leu Ile
    160                 165                 170 gca ctt gat gct gca gaa gag ttc ttt aag taa gct cgt cga act tac      636
Ala Leu Asp Ala Ala Glu Glu Phe Phe Lys     Ala Arg Arg Thr Tyr
175                 180             185 ccc aag aag cct ggg gtt cca tgc ctg gca gat ggc cag aaa taa ctg      684
Pro Lys Lys Pro Gly Val Pro Cys Leu Ala Asp Gly Gln Lys     Leu
190                 195                 200 cac tac ctt ccg ttt cca agt ccc gggaattcat cgtgactgac tgacgatctg      738
His Tyr Leu Pro Phe Pro Ser Pro
205                 210
```

```
cctcgcgcgt tcggtgatg acggtgaaaa cctctgacac atgcagctcc cggagacggt      798
cacagcttgt ctgtaagcgg atgccgggag cagacaagcc cgtcaggcgc gtcagcgggt      858
gttggcgggt gtcgggcgc agccatgacc cagtcacgta gcgatagcgg agtgtataaa      918
ttcttgaagr acg                                                        931
```

<210> SEQ ID NO 28
<211> LENGTH: 184
<212> TYPE: PRT
<213> ORGANISM: Artificial sequence
<220> FEATURE:
<223> OTHER INFORMATION: Synthetic Construct

<400> SEQUENCE: 28

```
Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
                20                  25                  30

Asp Asn Asn Pro Tyr Ser Ser Phe Gly Ala Thr Leu Val Arg Asp Asp
            35                  40                  45

Glu Lys Asn Leu Trp Ser Met Pro His Asp Val Ser His Thr Glu Ala
        50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn His Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
    130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys
            180
```

<210> SEQ ID NO 29
<211> LENGTH: 19
<212> TYPE: PRT
<213> ORGANISM: Artificial sequence
<220> FEATURE:
<223> OTHER INFORMATION: Synthetic Construct

<400> SEQUENCE: 29

```
Ala Arg Arg Thr Tyr Pro Lys Lys Pro Gly Val Pro Cys Leu Ala Asp
1               5                   10                  15

Gly Gln Lys
```

<210> SEQ ID NO 30
<211> LENGTH: 9
<212> TYPE: PRT
<213> ORGANISM: Artificial sequence
<220> FEATURE:
<223> OTHER INFORMATION: Synthetic Construct

<400> SEQUENCE: 30

Leu His Tyr Leu Pro Phe Pro Ser Pro
1               5

<210> SEQ ID NO 31
<211> LENGTH: 924
<212> TYPE: DNA
<213> ORGANISM: Artificial sequence
<220> FEATURE:
<223> OTHER INFORMATION: USMREGDelta20, Clone #1
<220> FEATURE:
<221> NAME/KEY: CDS
<222> LOCATION: (57)..(836)

<400> SEQUENCE: 31

```
tsttacattt ccacaggaac agtattcatg gggctgaggg actggaaaca gtattc atg      59
                                                              Met
                                                              1 ggg ctg agg gac tgg ctg aga acc gtg tgc tgc tgc tgc ggg tgc gag       107
Gly Leu Arg Asp Trp Leu Arg Thr Val Cys Cys Cys Cys Gly Cys Glu
        5                   10                  15 tgc ttg gag gag cgc gcc ctg cct gag aag gag ccc ctc gtc agt gat       155
Cys Leu Glu Glu Arg Ala Leu Pro Glu Lys Glu Pro Leu Val Ser Asp
    20                  25                  30 aac aat cca tat tcc tca ttt gga gca act ctg gtg agg gat gat gag       203
Asn Asn Pro Tyr Ser Ser Phe Gly Ala Thr Leu Val Arg Asp Asp Glu
35                  40                  45 aag aat tta tgg agt atg ccc cat gat gtg tcc cac aca gag gca gac       251
Lys Asn Leu Trp Ser Met Pro His Asp Val Ser His Thr Glu Ala Asp
50                  55                  60                  65 gac gac aga acc ctg tac aat ttg ata gtc att cgt aat cag cag gcc       299
Asp Asp Arg Thr Leu Tyr Asn Leu Ile Val Ile Arg Asn Gln Gln Ala
                70                  75                  80 aaa gac tca gag gag tgg cag aag ctc aac tat gat atc cat acc ctg       347
Lys Asp Ser Glu Glu Trp Gln Lys Leu Asn Tyr Asp Ile His Thr Leu
            85                  90                  95 cgg cag gtt cga agg gaa gta aga aac aga tgg aag tgc atc tta gaa       395
Arg Gln Val Arg Arg Glu Val Arg Asn Arg Trp Lys Cys Ile Leu Glu
        100                 105                 110 gat tta ggt ttt caa aag gaa gct gac tct ttg ttg tca gtg act aaa       443
Asp Leu Gly Phe Gln Lys Glu Ala Asp Ser Leu Leu Ser Val Thr Lys
    115                 120                 125 ctc agc acc atc agt gat tct aaa aac aca agg aaa gct cga gag atg       491
Leu Ser Thr Ile Ser Asp Ser Lys Asn Thr Arg Lys Ala Arg Glu Met
130                 135                 140                 145 ttg tta aaa ctg gct gaa gaa acc aat att ttc cca aca agt tgg gag       539
Leu Leu Lys Leu Ala Glu Glu Thr Asn Ile Phe Pro Thr Ser Trp Glu
                150                 155                 160 ctc tca gag aga tat ctc ttt gtt gtg gac cgt ctc att gca ctt gat       587
Leu Ser Glu Arg Tyr Leu Phe Val Val Asp Arg Leu Ile Ala Leu Asp
            165                 170                 175 gct gca gag gag ttc ttt aag ctt gct cgt cga act tac ccc aag aag       635
Ala Ala Glu Glu Phe Phe Lys Leu Ala Arg Arg Thr Tyr Pro Lys Lys
        180                 185                 190 ccc atg gtt cca tgc ctg gcc caa gaa gcc cat ggt tcc atg cct ggc       683
Pro Met Val Pro Cys Leu Ala Gln Glu Ala His Gly Ser Met Pro Gly
    195                 200                 205 aga tgg cca gaa aga act gca cta cct tcc gtt tcc aag tcc cat ggc       731
Arg Trp Pro Glu Arg Thr Ala Leu Pro Ser Val Ser Lys Ser His Gly
210                 215                 220                 225 ccc tat act agg tta ttg gaa aat taa ggg cct tgt gca acc cac tcg       779
Pro Tyr Thr Arg Leu Leu Glu Asn     Gly Pro Cys Ala Thr His Ser
```

```
                         230                 235                 240
act tct ttt gga ata tct tga aga aaa ata tga aga gca ttt gta tga      827
Thr Ser Phe Gly Ile Ser     Arg Lys Ile     Arg Ala Phe Val
                245                         250 gcg cga tga agtgataatg gcgaaacaaa aagttgatgg ttggagttcc              876
Ala Arg
    255 atctctatat atgatggtga tgtaattaac acagtctatg gccatcat                 924
```

<210> SEQ ID NO 32
<211> LENGTH: 233
<212> TYPE: PRT
<213> ORGANISM: Artificial sequence
<220> FEATURE:
<223> OTHER INFORMATION: Synthetic Construct

<400> SEQUENCE: 32

```
Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
            20                  25                  30

Asp Asn Pro Tyr Ser Ser Phe Gly Ala Thr Leu Val Arg Asp Asp
        35                  40                  45

Glu Lys Asn Leu Trp Ser Met Pro His Asp Val Ser His Thr Glu Ala
    50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn Tyr Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
    130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys Leu Ala Arg Arg Thr Tyr Pro Lys
            180                 185                 190

Lys Pro Met Val Pro Cys Leu Ala Gln Glu Ala His Gly Ser Met Pro
        195                 200                 205

Gly Arg Trp Pro Glu Arg Thr Ala Leu Pro Ser Val Ser Lys Ser His
    210                 215                 220

Gly Pro Tyr Thr Arg Leu Leu Glu Asn
225                 230
```

<210> SEQ ID NO 33
<211> LENGTH: 13
<212> TYPE: PRT
<213> ORGANISM: Artificial sequence
<220> FEATURE:
<223> OTHER INFORMATION: Synthetic Construct

<400> SEQUENCE: 33

```
Gly Pro Cys Ala Thr His Ser Thr Ser Phe Gly Ile Ser
1               5                   10
```

<210> SEQ ID NO 34
<211> LENGTH: 4
<212> TYPE: PRT
<213> ORGANISM: Artificial sequence
<220> FEATURE:
<223> OTHER INFORMATION: Synthetic Construct

<400> SEQUENCE: 34

Arg Ala Phe Val
 1

<210> SEQ ID NO 35
<211> LENGTH: 952
<212> TYPE: DNA
<213> ORGANISM: Artificial sequence
<220> FEATURE:
<223> OTHER INFORMATION: USMREGDelta30, cloine #1
<220> FEATURE:
<221> NAME/KEY: CDS
<222> LOCATION: (346)..(951)

<400> SEQUENCE: 35

```
tgttgatgaa agctggctac aggaaggccc agacgcgaat tattttttgat gcgtggaatt      60 agctatcgac tgcacggtgc accaatgctt ctggcgtcag gcagccatcg gaagctgtgg     120
tatggctgtg caggtcgtaa atcactgcat aattcgtgtc gctcaaggcg cactcccgtt     180
ctggataatg tttttttgcgc cgacatcata acggttctgg caaatattct gaaatgagct     240
gttgacaatt aatcatcggc tcgtataatg tgtggaattg tgagcggata acaatttcac     300
acaggaaaca gtattcatgg ggctgaggga ctggaaacag tattc atg ggg ctg agg      357
                                                  Met Gly Leu Arg
                                                    1 gac tgg ctg aga acc gtg tgc tgc tgc ggg tgc gag tgc ttg gag           405
Asp Trp Leu Arg Thr Val Cys Cys Cys Gly Cys Glu Cys Leu Glu
 5                  10                  15                  20 gag cgc gcc ctg cct gag aag gag ccc ctc gtc agt gat aac aat cca       453
Glu Arg Ala Leu Pro Glu Lys Glu Pro Leu Val Ser Asp Asn Asn Pro
                 25                  30                  35 tat tcc tca ttt gga gca act ctg gtg agg gat gat gag aag aat tta      501
Tyr Ser Ser Phe Gly Ala Thr Leu Val Arg Asp Asp Glu Lys Asn Leu
             40                  45                  50 tgg agt atg ccc cat gat gtg tcc cac aca gag gca gac gac gac aga      549
Trp Ser Met Pro His Asp Val Ser His Thr Glu Ala Asp Asp Asp Arg
         55                  60                  65 acc ctg tac aat ttg ata gtc att cgt aat cag cag gcc aaa gac tca      597
Thr Leu Tyr Asn Leu Ile Val Ile Arg Asn Gln Gln Ala Lys Asp Ser
     70                  75                  80 gag gag tgg cag aag ctc aac tat gat atc cat acc ctg cgg cag gtt      645
Glu Glu Trp Gln Lys Leu Asn Tyr Asp Ile His Thr Leu Arg Gln Val
 85                  90                  95                 100 cga agg gaa gta aga aac aga tgg aag tgc atc tta gaa gat tta ggt      693
Arg Arg Glu Val Arg Asn Arg Trp Lys Cys Ile Leu Glu Asp Leu Gly
                105                 110                 115 ttt caa aag gaa gct gac tct ttg ttg tca gtg act aaa ctc agc acc      741
Phe Gln Lys Glu Ala Asp Ser Leu Leu Ser Val Thr Lys Leu Ser Thr
            120                 125                 130 atc agt gat tct aaa aac aca agg aaa gct cga gag atg ttg tta aaa      789
Ile Ser Asp Ser Lys Asn Thr Arg Lys Ala Arg Glu Met Leu Leu Lys
        135                 140                 145 ctg gct gaa gaa acc aat att ttc cca aca agt tgg gag ctc tca gag      837
Leu Ala Glu Glu Thr Asn Ile Phe Pro Thr Ser Trp Glu Leu Ser Glu
```

```
aga tat ctc ttt gtt gtg gac cgt ctc att gca ctt gat gct gca gaa      885
Arg Tyr Leu Phe Val Val Asp Arg Leu Ile Ala Leu Asp Ala Ala Glu
165                 170                 175                 180 gag ttc ttt acc atg gcc cct ata cta ggt tat tgg aaa att aag ggc      933
Glu Phe Phe Thr Met Ala Pro Ile Leu Gly Tyr Trp Lys Ile Lys Gly
                185                 190                 195 ctg tgc aac cca ctc gaa t                                            952
Leu Cys Asn Pro Leu Glu
            200
```

<210> SEQ ID NO 36
<211> LENGTH: 202
<212> TYPE: PRT
<213> ORGANISM: Artificial sequence
<220> FEATURE:
<223> OTHER INFORMATION: Synthetic Construct

<400> SEQUENCE: 36

```
Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
                20                  25                  30

Asp Asn Asn Pro Tyr Ser Ser Phe Gly Ala Thr Leu Val Arg Asp Asp
            35                  40                  45

Glu Lys Asn Leu Trp Ser Met Pro His Asp Val Ser His Thr Glu Ala
    50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn Tyr Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Thr Met Ala Pro Ile Leu Gly Tyr Trp
            180                 185                 190

Lys Ile Lys Gly Leu Cys Asn Pro Leu Glu
        195                 200
```

<210> SEQ ID NO 37
<211> LENGTH: 23
<212> TYPE: DNA
<213> ORGANISM: Artificial sequence
<220> FEATURE:
<223> OTHER INFORMATION: DS MREG forward primer

<400> SEQUENCE: 37
gggctggcaa gccacgtttg gtg                                            23

<210> SEQ ID NO 38
<211> LENGTH: 23
<212> TYPE: DNA

```
<213> ORGANISM: Artificial sequence
<220> FEATURE:
<223> OTHER INFORMATION: DSMREGDelta 10 reverse primer

<400> SEQUENCE: 38
ccgggagctg catgtgtcag agg                                          23

<210> SEQ ID NO 39
<211> LENGTH: 21
<212> TYPE: DNA
<213> ORGANISM: Artificial sequence
<220> FEATURE:
<223> OTHER INFORMATION: US MREG forward primer

<400> SEQUENCE: 39
ycatcggctc gtataatgtg t                                            21

<210> SEQ ID NO 40
<211> LENGTH: 23
<212> TYPE: DNA
<213> ORGANISM: Artificial sequence
<220> FEATURE:
<223> OTHER INFORMATION: US MREG reverse primer

<400> SEQUENCE: 40
ccgggagctg catgtgtcag agg                                          23

<210> SEQ ID NO 41
<211> LENGTH: 18
<212> TYPE: DNA
<213> ORGANISM: Artificial sequence
<220> FEATURE:
<223> OTHER INFORMATION: Mus musculus (N-terminal GFP) forward primer

<400> SEQUENCE: 41
agcttcccga ctaccact                                                18

<210> SEQ ID NO 42
<211> LENGTH: 19
<212> TYPE: DNA
<213> ORGANISM: Artificial sequence
<220> FEATURE:
<223> OTHER INFORMATION: Mus musculus N-terminal GFP reverse primer

<400> SEQUENCE: 42
cagtgcagtt ttctctggc                                               19

<210> SEQ ID NO 43
<211> LENGTH: 18
<212> TYPE: DNA
<213> ORGANISM: Artificial sequence
<220> FEATURE:
<223> OTHER INFORMATION: C-terminal GFP reverse primer

<400> SEQUENCE: 43
atcctggggc ttggaaat                                                18

<210> SEQ ID NO 44
<211> LENGTH: 642
<212> TYPE: DNA
<213> ORGANISM: Artificial sequence
<220> FEATURE:
<223> OTHER INFORMATION: L90A mutation on mMREG
<220> FEATURE:
<221> NAME/KEY: CDS
<222> LOCATION: (1)..(642)
```

<400> SEQUENCE: 44

```
atg ggg ctg cgc cgc tgg cta cgg agc gcc tgc tgc tgc ccg tgc        48
Met Gly Leu Arg Arg Trp Leu Arg Ser Ala Cys Cys Cys Pro Cys
1               5                   10                  15 cgg tgc ctg gag gag ccc gcg cgg ccc gag aag gag ccg ctg gtc agt    96
Arg Cys Leu Glu Glu Pro Ala Arg Pro Glu Lys Glu Pro Leu Val Ser
                20                  25                  30 ggt aac aat ccg tat tcc tcc ttt gga gcg act ctg gag agg gat gat   144
Gly Asn Asn Pro Tyr Ser Ser Phe Gly Ala Thr Leu Glu Arg Asp Asp
            35                  40                  45 gag aag aat tta tgg agc atg cct cat gac gtg tcc cac aca gag gcg   192
Glu Lys Asn Leu Trp Ser Met Pro His Asp Val Ser His Thr Glu Ala
        50                  55                  60 gat gac gat agg atc ttg tat aat ttg ata gtc att cgt aat cag cag   240
Asp Asp Asp Arg Ile Leu Tyr Asn Leu Ile Val Ile Arg Asn Gln Gln
65                  70                  75                  80 acc aaa gac tca gag gaa tgg caa aga gcc aac tat gat atc tac acc   288
Thr Lys Asp Ser Glu Glu Trp Gln Arg Ala Asn Tyr Asp Ile Tyr Thr
                85                  90                  95 ctg cgg cag atc cgc agg gaa gtg agg aac cga tgg aga cga atc tta   336
Leu Arg Gln Ile Arg Arg Glu Val Arg Asn Arg Trp Arg Arg Ile Leu
            100                 105                 110 gag gac ttg ggc ttt caa agg gaa gcc gac tct ctg ttg tca gtg acc   384
Glu Asp Leu Gly Phe Gln Arg Glu Ala Asp Ser Leu Leu Ser Val Thr
        115                 120                 125 aaa ctc agc acc atg agt gat tct aaa aac aca agg aaa gcc cgg gag   432
Lys Leu Ser Thr Met Ser Asp Ser Lys Asn Thr Arg Lys Ala Arg Glu
130                 135                 140 atg ctg tta aag ctg gct gaa gag acc tct atc ttc ccc gcc agc tgg   480
Met Leu Leu Lys Leu Ala Glu Glu Thr Ser Ile Phe Pro Ala Ser Trp
145                 150                 155                 160 gag ctc tcc gag agg tac ctc ttg gtt gtg gac cgg ctc att gct ctc   528
Glu Leu Ser Glu Arg Tyr Leu Leu Val Val Asp Arg Leu Ile Ala Leu
                165                 170                 175 gat gct gct gag gac ttc ttt aag att gct agc caa atg tac ccc aag   576
Asp Ala Ala Glu Asp Phe Phe Lys Ile Ala Ser Gln Met Tyr Pro Lys
            180                 185                 190 aaa cct ggg gtc cca tgc ctg gtg gac ggc cag aga aaa ctg cac tgc   624
Lys Pro Gly Val Pro Cys Leu Val Asp Gly Gln Arg Lys Leu His Cys
        195                 200                 205 ctt cca ttt cca agc ccc                                           642
Leu Pro Phe Pro Ser Pro
        210
```

<210> SEQ ID NO 45
<211> LENGTH: 214
<212> TYPE: PRT
<213> ORGANISM: Artificial sequence
<220> FEATURE:
<223> OTHER INFORMATION: Synthetic Construct

<400> SEQUENCE: 45

```
Met Gly Leu Arg Arg Trp Leu Arg Ser Ala Cys Cys Cys Pro Cys
1               5                   10                  15

Arg Cys Leu Glu Glu Pro Ala Arg Pro Glu Lys Glu Pro Leu Val Ser
                20                  25                  30

Gly Asn Asn Pro Tyr Ser Ser Phe Gly Ala Thr Leu Glu Arg Asp Asp
            35                  40                  45

Glu Lys Asn Leu Trp Ser Met Pro His Asp Val Ser His Thr Glu Ala
        50                  55                  60
```

-continued

```
Asp Asp Asp Arg Ile Leu Tyr Asn Leu Ile Val Ile Arg Asn Gln Gln
 65                  70                  75                  80

Thr Lys Asp Ser Glu Glu Trp Gln Arg Ala Asn Tyr Asp Ile Tyr Thr
                 85                  90                  95

Leu Arg Gln Ile Arg Arg Glu Val Arg Asn Arg Trp Arg Arg Ile Leu
            100                 105                 110

Glu Asp Leu Gly Phe Gln Arg Glu Ala Asp Ser Leu Leu Ser Val Thr
        115                 120                 125

Lys Leu Ser Thr Met Ser Asp Ser Lys Asn Thr Arg Lys Ala Arg Glu
130                 135                 140

Met Leu Leu Lys Leu Ala Glu Glu Thr Ser Ile Phe Pro Ala Ser Trp
145                 150                 155                 160

Glu Leu Ser Glu Arg Tyr Leu Leu Val Val Asp Arg Leu Ile Ala Leu
                165                 170                 175

Asp Ala Ala Glu Asp Phe Phe Lys Ile Ala Ser Gln Met Tyr Pro Lys
            180                 185                 190

Lys Pro Gly Val Pro Cys Leu Val Asp Gly Gln Arg Lys Leu His Cys
        195                 200                 205

Leu Pro Phe Pro Ser Pro
    210
```

<210> SEQ ID NO 46
<211> LENGTH: 18
<212> TYPE: DNA
<213> ORGANISM: Artificial sequence
<220> FEATURE:
<223> OTHER INFORMATION: Mus musculus GFP-MREG (W87A) forward rpimer

<400> SEQUENCE: 46
agcttcccga ctaccact                                                    18

<210> SEQ ID NO 47
<211> LENGTH: 19
<212> TYPE: DNA
<213> ORGANISM: Artificial sequence
<220> FEATURE:
<223> OTHER INFORMATION: GFP-MREG (W87A) Clone #1010 Primers (N-terminal
      GFP):

<400> SEQUENCE: 47
cagtgcagtt ttctctggc                                                   19

<210> SEQ ID NO 48
<211> LENGTH: 18
<212> TYPE: DNA
<213> ORGANISM: Artificial sequence
<220> FEATURE:
<223> OTHER INFORMATION: GFP-MREG C-terminal GFP reverse primer

<400> SEQUENCE: 48
atcctggggc ttggaaat                                                    18

<210> SEQ ID NO 49
<211> LENGTH: 642
<212> TYPE: DNA
<213> ORGANISM: Artificial sequence
<220> FEATURE:
<223> OTHER INFORMATION: W87A mutation on mMREG
<220> FEATURE:
<221> NAME/KEY: CDS
<222> LOCATION: (1)..(642)

```
<400> SEQUENCE: 49 atg ggg ctg cgc cgc tgg cta cgg agc gcc tgc tgc tgc ccg tgc        48
Met Gly Leu Arg Arg Trp Leu Arg Ser Ala Cys Cys Cys Pro Cys
1               5                   10                  15 cgg tgc ctg gag gag ccc gcg cgg ccc gag aag gag ccg ctg gtc agt    96
Arg Cys Leu Glu Glu Pro Ala Arg Pro Glu Lys Glu Pro Leu Val Ser
            20                  25                  30 ggt aac aat ccg tat tcc tcc ttt gga gcg act ctg gag agg gat gat    144
Gly Asn Asn Pro Tyr Ser Ser Phe Gly Ala Thr Leu Glu Arg Asp Asp
        35                  40                  45 gag aag aat tta tgg agc atg cct cat gac gtg tcc cac aca gag gcg    192
Glu Lys Asn Leu Trp Ser Met Pro His Asp Val Ser His Thr Glu Ala
50                  55                  60 gat gac gat agg atc ttg tat aat ttg ata gtc att cgt aat cag cag    240
Asp Asp Asp Arg Ile Leu Tyr Asn Leu Ile Val Ile Arg Asn Gln Gln
65                  70                  75                  80 acc aaa gac tca gag gaa gcg caa aga ctc aac tat gat atc tac acc    288
Thr Lys Asp Ser Glu Glu Ala Gln Arg Leu Asn Tyr Asp Ile Tyr Thr
                85                  90                  95 ctg cgg cag atc cgc agg gaa gtg agg aac cga tgg aga cga atc tta    336
Leu Arg Gln Ile Arg Arg Glu Val Arg Asn Arg Trp Arg Arg Ile Leu
            100                 105                 110 gag gac ttg ggc ttt caa agg gaa gcc gac tct ctg ttg tca gtg acc    384
Glu Asp Leu Gly Phe Gln Arg Glu Ala Asp Ser Leu Leu Ser Val Thr
        115                 120                 125 aaa ctc agc acc atg agt gat tct aaa aac aca agg aaa gcc cgg gag    432
Lys Leu Ser Thr Met Ser Asp Ser Lys Asn Thr Arg Lys Ala Arg Glu
130                 135                 140 atg ctg tta aag ctg gct gaa gag acc tct atc ttc ccc gcc agc tgg    480
Met Leu Leu Lys Leu Ala Glu Glu Thr Ser Ile Phe Pro Ala Ser Trp
145                 150                 155                 160 gag ctc tcc gag agg tac ctc ttg gtt gtg gac cgg ctc att gct ctc    528
Glu Leu Ser Glu Arg Tyr Leu Leu Val Val Asp Arg Leu Ile Ala Leu
                165                 170                 175 gat gct gct gag gac ttc ttt aag att gct agc caa atg tac ccc aag    576
Asp Ala Ala Glu Asp Phe Phe Lys Ile Ala Ser Gln Met Tyr Pro Lys
            180                 185                 190 aaa cct ggg gtc cca tgc ctg gtg gac ggc cag aga aaa ctg cac tgc    624
Lys Pro Gly Val Pro Cys Leu Val Asp Gly Gln Arg Lys Leu His Cys
        195                 200                 205 ctt cca ttt cca agc ccc                                            642
Leu Pro Phe Pro Ser Pro
        210

<210> SEQ ID NO 50
<211> LENGTH: 214
<212> TYPE: PRT
<213> ORGANISM: Artificial sequence
<220> FEATURE:
<223> OTHER INFORMATION: Synthetic Construct

<400> SEQUENCE: 50

Met Gly Leu Arg Arg Trp Leu Arg Ser Ala Cys Cys Cys Pro Cys
1               5                   10                  15

Arg Cys Leu Glu Glu Pro Ala Arg Pro Glu Lys Glu Pro Leu Val Ser
            20                  25                  30

Gly Asn Asn Pro Tyr Ser Ser Phe Gly Ala Thr Leu Glu Arg Asp Asp
        35                  40                  45

Glu Lys Asn Leu Trp Ser Met Pro His Asp Val Ser His Thr Glu Ala
50                  55                  60
```

Asp Asp Asp Arg Ile Leu Tyr Asn Leu Ile Val Ile Arg Asn Gln Gln
65                  70                  75                  80

Thr Lys Asp Ser Glu Glu Ala Gln Arg Leu Asn Tyr Asp Ile Tyr Thr
                85                  90                  95

Leu Arg Gln Ile Arg Arg Glu Val Arg Asn Arg Trp Arg Arg Ile Leu
            100                 105                 110

Glu Asp Leu Gly Phe Gln Arg Glu Ala Asp Ser Leu Leu Ser Val Thr
        115                 120                 125

Lys Leu Ser Thr Met Ser Asp Ser Lys Asn Thr Arg Lys Ala Arg Glu
    130                 135                 140

Met Leu Leu Lys Leu Ala Glu Glu Thr Ser Ile Phe Pro Ala Ser Trp
145                 150                 155                 160

Glu Leu Ser Glu Arg Tyr Leu Leu Val Val Asp Arg Leu Ile Ala Leu
                165                 170                 175

Asp Ala Ala Glu Asp Phe Phe Lys Ile Ala Ser Gln Met Tyr Pro Lys
            180                 185                 190

Lys Pro Gly Val Pro Cys Leu Val Asp Gly Gln Arg Lys Leu His Cys
        195                 200                 205

Leu Pro Phe Pro Ser Pro
    210

<210> SEQ ID NO 51
<211> LENGTH: 941
<212> TYPE: DNA
<213> ORGANISM: Artificial sequence
<220> FEATURE:
<223> OTHER INFORMATION: DS MREGdelta 9pGEXhMREGdelta20, clone #6)
<220> FEATURE:
<221> NAME/KEY: CDS
<222> LOCATION: (255)..(896)

<400> SEQUENCE: 51
ggtgatcatt aagccatcat gacgtcagat gtatgctctt gatgtgttgt atacatgacc    60
catgtgcctg gatgcgtcca aatgttgttt aaaaaacgta ttgaagcttc cacaaattga   120
taagtacttg aatccagcaa gtatatagca tggcctttgc aggctggcaa gccacgtttg   180
gtggtgtgac catcatccaa aatcggatct ggttccggtg gatccccggg gctgagggac   240
tggaaacagt attc atg ggg ctg agg gac tgg ctg aga acc gtg tgc tgc    290
              Met Gly Leu Arg Asp Trp Leu Arg Thr Val Cys Cys
                1               5                   10 tgc tgc ggg tgc gag tgc ttg gag gag cgc gcc ctg cct gag aag gag    338
Cys Cys Gly Cys Glu Cys Leu Glu Glu Arg Ala Leu Pro Glu Lys Glu
        15                  20                  25 ccc ctc gtc agt gat aac aat cca tat tcc tca ttt gga gca act ctg    386
Pro Leu Val Ser Asp Asn Asn Pro Tyr Ser Ser Phe Gly Ala Thr Leu
    30                  35                  40 gtg agg gat gat gag aag aat tta tgg agt atg ccc cat gat gtg tcc    434
Val Arg Asp Asp Glu Lys Asn Leu Trp Ser Met Pro His Asp Val Ser
45                  50                  55                  60 cac aca gag gca gac gac gac aga acc ctg tac aat ttg ata gtc att    482
His Thr Glu Ala Asp Asp Asp Arg Thr Leu Tyr Asn Leu Ile Val Ile
                65                  70                  75 cgt aat cag cag gcc aaa gac tca gag gag tgg cag aag ctc aac cat    530
Arg Asn Gln Gln Ala Lys Asp Ser Glu Glu Trp Gln Lys Leu Asn His
            80                  85                  90 gat atc cat acc ctg cgg cag gtt cga agg gaa gta aga aac aga tgg    578
Asp Ile His Thr Leu Arg Gln Val Arg Arg Glu Val Arg Asn Arg Trp
        95                  100                 105

```
aag tgc atc tta gaa gat tta ggt ttt caa aag gaa gct gac tct ttg      626
Lys Cys Ile Leu Glu Asp Leu Gly Phe Gln Lys Glu Ala Asp Ser Leu
    110                 115                 120 ttg tca gtg act aaa ctc agc acc atc agt gat tct aaa aac aca agg      674
Leu Ser Val Thr Lys Leu Ser Thr Ile Ser Asp Ser Lys Asn Thr Arg
125                 130                 135                 140 aaa gct cga gag atg ttg tta aaa ctg gct gaa gaa acc aat att ttc      722
Lys Ala Arg Glu Met Leu Leu Lys Leu Ala Glu Glu Thr Asn Ile Phe
                145                 150                 155 cca aca agt tgg gag ctc tca gag aga tat ctc ttt gtt gtg gac cgt      770
Pro Thr Ser Trp Glu Leu Ser Glu Arg Tyr Leu Phe Val Val Asp Arg
            160                 165                 170 ctc att gca ctt gat gct gca gag gag ttc ttt aag ctt gct cgt cga      818
Leu Ile Ala Leu Asp Ala Ala Glu Glu Phe Phe Lys Leu Ala Arg Arg
        175                 180                 185 act tac ccc aag aag cct taa gtt cca tgc ctg gca gat ggc cag aaa      866
Thr Tyr Pro Lys Lys Pro     Val Pro Cys Leu Ala Asp Gly Gln Lys
    190             195                 200 taa ctg cac tac ctt ccg ttt cca agt ccc gggaattcat cgtgactgac        916
    Leu His Tyr Leu Pro Phe Pro Ser Pro
    205                 210 tgacgatctg cctcgcgcgt tcgaa                                          941
```

<210> SEQ ID NO 52
<211> LENGTH: 194
<212> TYPE: PRT
<213> ORGANISM: Artificial sequence
<220> FEATURE:
<223> OTHER INFORMATION: Synthetic Construct

<400> SEQUENCE: 52

```
Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
            20                  25                  30

Asp Asn Asn Pro Tyr Ser Ser Phe Gly Ala Thr Leu Val Arg Asp Asp
        35                  40                  45

Glu Lys Asn Leu Trp Ser Met Pro His Asp Val Ser His Thr Glu Ala
    50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn His Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
    130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys Leu Ala Arg Arg Thr Tyr Pro Lys
            180                 185                 190

Lys Pro
```

<210> SEQ ID NO 53
<211> LENGTH: 9
<212> TYPE: PRT
<213> ORGANISM: Artificial sequence
<220> FEATURE:
<223> OTHER INFORMATION: Synthetic Construct

<400> SEQUENCE: 53

Val Pro Cys Leu Ala Asp Gly Gln Lys
1               5

<210> SEQ ID NO 54
<211> LENGTH: 9
<212> TYPE: PRT
<213> ORGANISM: Artificial sequence
<220> FEATURE:
<223> OTHER INFORMATION: Synthetic Construct

<400> SEQUENCE: 54

Leu His Tyr Leu Pro Phe Pro Ser Pro
1               5

<210> SEQ ID NO 55
<211> LENGTH: 214
<212> TYPE: PRT
<213> ORGANISM: Homo sapiens

<400> SEQUENCE: 55

Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
                20                  25                  30

Asp Asn Asn Pro Tyr Ser Ser Phe Gly Ala Thr Leu Val Arg Asp Asp
            35                  40                  45

Glu Lys Asn Leu Trp Ser Met Pro His Asp Val Ser His Thr Glu Ala
50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn Tyr Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys Leu Ala Arg Arg Thr Tyr Pro Lys
            180                 185                 190

Lys Pro Gly Val Pro Cys Leu Ala Asp Gly Gln Lys Glu Leu His Tyr
        195                 200                 205

Leu Pro Phe Pro Ser Pro
        210

<210> SEQ ID NO 56
<211> LENGTH: 224

```
<212> TYPE: PRT
<213> ORGANISM: Homo sapiens

<400> SEQUENCE: 56

Met Gly Leu Arg Asp Trp Leu Arg Thr Val Cys Cys Cys Gly Cys
1               5                   10                  15

Glu Cys Leu Glu Glu Arg Ala Leu Pro Glu Lys Glu Pro Leu Val Ser
            20                  25                  30

Asp Asn Asn Pro Tyr Ser Ser Phe Gly Ala Thr Leu Val Arg Asp Asp
                35                  40                  45

Glu Lys Asn Leu Trp Ser Met Pro His Asp Val Ser His Thr Glu Ala
        50                  55                  60

Asp Asp Asp Arg Thr Leu Tyr Asn Leu Ile Val Ile Arg Asn Gln Gln
65                  70                  75                  80

Ala Lys Asp Ser Glu Glu Trp Gln Lys Leu Asn Tyr Asp Ile His Thr
                85                  90                  95

Leu Arg Gln Val Arg Arg Glu Val Arg Asn Arg Trp Lys Cys Ile Leu
            100                 105                 110

Glu Asp Leu Gly Phe Gln Lys Glu Ala Asp Ser Leu Leu Ser Val Thr
        115                 120                 125

Lys Leu Ser Thr Ile Ser Asp Ser Lys Asn Thr Arg Lys Ala Arg Glu
    130                 135                 140

Met Leu Leu Lys Leu Ala Glu Glu Thr Asn Ile Phe Pro Thr Ser Trp
145                 150                 155                 160

Glu Leu Ser Glu Arg Tyr Leu Phe Val Val Asp Arg Leu Ile Ala Leu
                165                 170                 175

Asp Ala Ala Glu Glu Phe Phe Lys Leu Ala Arg Arg Thr Tyr Pro Lys
            180                 185                 190

Lys Pro Gly Val Pro Cys Leu Ala Asp Gly Gln Lys Leu His Leu
        195                 200                 205

Trp Gly Asp Leu Ser Cys Arg Leu Ala His Met Gln Gly Val Leu His
210                 215                 220

<210> SEQ ID NO 57
<211> LENGTH: 204
<212> TYPE: PRT
<213> ORGANISM: Artificial Sequence
<220> FEATURE:
<223> OTHER INFORMATION: Engineered mutant MREG protein US Delta10

<400> SEQUENCE: 57

Cys Cys Cys Cys Gly Cys Glu Cys Leu Glu Glu Arg Ala Leu Pro Glu
1               5                   10                  15

Lys Glu Pro Leu Val Ser Asp Asn Asn Pro Tyr Ser Ser Phe Gly Ala
            20                  25                  30

Thr Leu Val Arg Asp Asp Glu Lys Asn Leu Trp Ser

```
            115                 120                 125
Thr Arg Lys Ala Arg Glu Met Leu Leu Lys Leu Ala Glu Glu Thr Asn
        130                 135                 140

Ile Phe Pro Thr Ser Trp Glu Leu Ser Glu Arg Tyr Leu Phe Val Val
145                 150                 155                 160

Asp Arg Leu Ile Ala Leu Asp Ala Ala Glu Phe Phe Lys Leu Ala
                165                 170                 175

Arg Arg Thr Tyr Pro Lys Lys Pro Gly Val Pro Cys Leu Ala Asp Gly
            180                 185                 190

Gln Lys Glu Leu His Tyr Leu Pro Phe Pro Ser Pro
            195                 200
```

<210> SEQ ID NO 58
<211> LENGTH: 194
<212> TYPE: PRT
<213> ORGANISM: Artificial sequence
<220> FEATURE:
<223> OTHER INFORMATION: Engineered mutant MREG US Delta 20

<400> SEQUENCE: 58

```
Glu Arg Ala Leu Pro Glu Lys Glu Pro Leu Val Ser Asp Asn Asn Pro
1               5                   10                  15

Tyr Ser Ser Phe Gly Ala Thr Leu Val Arg Asp Asp Glu Lys Asn Leu
                20                  25                  30

Trp Ser Met Pro His Asp Val Ser His Thr Glu Ala Asp Asp Arg
            35                  40                  45

Thr Leu Tyr Asn Leu Ile Val Ile Arg Asn Gln Gln Ala Lys Asp Ser
    50                  55                  60

Glu Glu Trp Gln Lys Leu Asn Tyr Asp Ile His Thr Leu Arg Gln Val
65                  70                  75                  80

Arg Arg Glu Val Arg Asn Arg Trp Lys Cys Ile Leu Glu Asp Leu Gly
                85                  90                  95

Phe Gln Lys Glu Ala Asp Ser Leu Leu Ser Val Thr Lys Leu Ser Thr
            100                 105                 110

Ile Ser Asp Ser Lys Asn Thr Arg Lys Ala Arg Glu Met Leu Leu Lys
        115                 120                 125

Leu Ala Glu Glu Thr Asn Ile Phe Pro Thr Trp Glu Leu Ser Glu
    130                 135                 140

Arg Tyr Leu Phe Val Val Asp Arg Leu Ile Ala Leu Asp Ala Ala Glu
145                 150                 155                 160

Glu Phe Phe Lys Leu Ala Arg Arg Thr Tyr Pro Lys Lys Pro Gly Val
                165                 170                 175

Pro Cys Leu Ala Asp Gly Gln Lys Glu Leu His Tyr Leu Pro Phe Pro
            180                 185                 190

Ser Pro
```

<210> SEQ ID NO 59
<211> LENGTH: 194
<212> TYPE: PRT
<213> ORGANISM: Artificial sequence
<220> FEATURE:
<223> OTHER INFORMATION: Engineered mutant MREG US Delta 30

<400> SEQUENCE: 59

```
Glu Arg Ala Leu Pro Glu Lys Glu Pro Leu Val Ser Asp Asn Asn Pro
1               5                   10                  15

Tyr Ser Ser Phe Gly Ala Thr Leu Val Arg Asp Asp Glu Lys Asn Leu
```

-continued

```
                    20                  25                  30
Trp Ser Met Pro His Asp Val Ser His Thr Glu Ala Asp Asp Arg
            35                  40                  45

Thr Leu Tyr Asn Leu Ile Val Ile Arg Asn Gln Gln Ala Lys Asp Ser
 50                  55                  60

Glu Glu Trp Gln Lys Leu Asn Tyr Asp Ile His Thr Leu Arg Gln Val
 65                  70                  75                  80

Arg Arg Glu Val Arg Asn Arg Trp Lys Cys Ile Leu Glu Asp Leu Gly
                    85                  90                  95

Phe Gln Lys Glu Ala Asp Ser Leu Leu Ser Val Thr Lys Leu Ser Thr
                100                 105                 110

Ile Ser Asp Ser Lys Asn Thr Arg Lys Ala Arg Glu Met Leu Leu Lys
            115                 120                 125

Leu Ala Glu Glu Thr Asn Ile Phe Pro Thr Ser Trp Glu Leu Ser Glu
    130                 135                 140

Arg Tyr Leu Phe Val Val Asp Arg Leu Ile Ala Leu Asp Ala Ala Glu
145                 150                 155                 160

Glu Phe Phe Lys Leu Ala Arg Arg Thr Tyr Pro Lys Lys Pro Gly Val
                165                 170                 175

Pro Cys Leu Ala Asp Gly Gln Lys Glu Leu His Tyr Leu Pro Phe Pro
            180                 185                 190

Ser Pro

<210> SEQ ID NO 60
<211> LENGTH: 194
<212> TYPE: PRT
<213> ORGANISM: Artificial sequence
<220> FEATURE:
<223> OTHER INFORMATION: Engineered mutant MREG DS Delta 10

<400> SEQUENCE: 60

Cys Cys Cys Cys Gly Cys Glu Cys Leu Glu Glu Arg Ala Leu Pro Glu
 1               5                  10                  15

Lys Glu Pro Leu Val Ser Asp Asn Asn Pro Tyr Ser Ser Phe Gly Ala
                20                  25                  30

Thr Leu Val Arg Asp Asp Glu Lys Asn Leu Trp Ser Met Pro His Asp
            35                  40                  45

Val Ser His Thr Glu Ala Asp Asp Arg Thr Leu Tyr Asn Leu Ile
 50                  55                  60

Val Ile Arg Asn Gln Gln Ala Lys Asp Ser Glu Glu Trp Gln Lys Leu
 65                  70                  75                  80

Asn Tyr Asp Ile His Thr Leu Arg Gln Val Arg Arg Glu Val Arg Asn
                85                  90                  95

Arg Trp Lys Cys Ile Leu Glu Asp Leu Gly Phe Gln Lys Glu Ala Asp
                100                 105                 110

Ser Leu Leu Ser Val Thr Lys Leu Ser Thr Ile Ser Asp Ser Lys Asn
            115                 120                 125

Thr Arg Lys Ala Arg Glu Met Leu Leu Lys Leu Ala Glu Glu Thr Asn
    130                 135                 140

Ile Phe Pro Thr Ser Trp Glu Leu Ser Glu Arg Tyr Leu Phe Val Val
145                 150                 155                 160

Asp Arg Leu Ile Ala Leu Asp Ala Ala Glu Phe Phe Lys Leu Ala
                165                 170                 175

Arg Arg Thr Tyr Pro Lys Lys Pro Gly Val Pro Cys Leu Ala Asp Gly
                180                 185                 190
```

Gln Lys

<210> SEQ ID NO 61
<211> LENGTH: 184
<212> TYPE: PRT
<213> ORGANISM: Artificial Sequence
<220> FEATURE:
<223> OTHER INFORMATION: Engineered mutant MREG DS Delta 20

<400> SEQUENCE: 61

Cys Cys Cys Cys Gly Cys Glu Cys Leu Glu Glu Arg Ala Leu Pro Glu
1               5                   10                  15

Lys Glu Pro Leu Val Ser Asp Asn Asn Pro Tyr Ser Ser Phe Gly Ala
            20                  25                  30

Thr Leu Val Arg Asp Asp Glu Lys Asn Leu Trp Ser Met Pro His Asp
        35                  40                  45

Val Ser His Thr Glu Ala Asp Asp Arg Thr Leu Tyr Asn Leu Ile
    50                  55                  60

Val Ile Arg Asn Gln Gln Ala Lys Asp Ser Glu Glu Trp Gln Lys Leu
65                  70                  75                  80

Asn Tyr Asp Ile His Thr Leu Arg Gln Val Arg Arg Glu Val Arg Asn
                85                  90                  95

Arg Trp Lys Cys Ile Leu Glu Asp Leu Gly Phe Gln Lys Glu Ala Asp
            100                 105                 110

Ser Leu Leu Ser Val Thr Lys Leu Ser Thr Ile Ser Asp Ser Lys Asn
        115                 120                 125

Thr Arg Lys Ala Arg Glu Met Leu Leu Lys Leu Ala Glu Glu Thr Asn
    130                 135                 140

Ile Phe Pro Thr Ser Trp Glu Leu Ser Glu Arg Tyr Leu Phe Val Val
145                 150                 155                 160

Asp Arg Leu Ile Ala Leu Asp Ala Ala Glu Glu Phe Phe Lys Leu Ala
                165                 170                 175

Arg Arg Thr Tyr Pro Lys Lys Pro
            180

<210> SEQ ID NO 62
<211> LENGTH: 184
<212> TYPE: PRT
<213> ORGANISM: Artificial sequence
<220> FEATURE:
<223> OTHER INFORMATION: Engineered mutant MREG DS Delta 30

<400> SEQUENCE: 62

Cys Cys Cys Cys Gly Cys Glu Cys Leu Glu Glu Arg Ala Leu Pro Glu
1               5                   10                  15

Lys Glu Pro Leu Val Ser Asp Asn Asn Pro Tyr Ser Ser Phe Gly Ala
            20                  25                  30

Thr Leu Val Arg Asp Asp Glu Lys Asn Leu Trp Ser Met Pro His Asp
        35                  40                  45

Val Ser His Thr Glu Ala Asp Asp Arg Thr Leu Tyr Asn Leu Ile
    50                  55                  60

Val Ile Arg Asn Gln Gln Ala Lys Asp Ser Glu Glu Trp Gln Lys Leu
65                  70                  75                  80

Asn Tyr Asp Ile His Thr Leu Arg Gln Val Arg Arg Glu Val Arg Asn
                85                  90                  95

Arg Trp Lys Cys Ile Leu Glu Asp Leu Gly Phe Gln Lys Glu Ala Asp
            100                 105                 110

```
Ser Leu Leu Ser Val Thr Lys Leu Ser Thr Ile Ser Asp Ser Lys Asn
        115                 120                 125

Thr Arg Lys Ala Arg Glu Met Leu Leu Lys Leu Ala Glu Glu Thr Asn
        130                 135                 140

Ile Phe Pro Thr Ser Trp Glu Leu Ser Glu Arg Tyr Leu Phe Val Val
145                 150                 155                 160

Asp Arg Leu Ile Ala Leu Asp Ala Ala Glu Glu Phe Phe Lys Leu Ala
                165                 170                 175

Arg Arg Thr Tyr Pro Lys Lys Pro
            180
```

The invention claimed is:

1. A recombinant adeno-associated viral (rAAV) vector useful in treating a subject with age-related macular degeneration and/or Stargardt's Disease which comprises an AAV capsid and a nucleic acid molecule packaged therein, wherein the nucleic acid molecule comprises a 5' AAV inverted terminal repeat (ITR) sequence, a nucleic acid sequence encoding a mutated melanoregulin (MREG) protein under the control of expression control sequences which direct expression of the mutated MREG protein in ocular cells of the subject's eye, and a 3' AAV ITR sequence, wherein the mutated MREG protein is:

(a) MREG USΔ10: SEQ ID NO: 57:
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKPGVPCLA

DGQK ELHYLP FPSP-$^C$, (b) MREG USΔ20: SEQ ID NO: 58:
$^N$-ERALPEKEPL VSDNNPYSSF GATLVRDDEK

NLWSMPHDVS HTEADDDRTL YNLIVIRNQQ AKDSEEWQKL

NYDIHTLRQV RREVRNRWKC ILEDLGFQKE ADSLLSVTKL

STISDSKNTR KAREMLLKLA EETNIFPTSW ELSERYLFVV

DRLIALDAAE EFFKLARRTY PKKPGVPCLA DGQKELHYLP

FPSP-$^C$, (c) MREG USΔ30: SEQ ID NO: 59:
$^N$-VSDNNPYSSF GATLVRDDEK NLWSMPHDVS

HTEADDDRTL YNLIVIRNQQ AKDSEEWQKL NYDIHTLRQV

RREVRNRWKC ILEDLGFQKE ADSLLSVTKL STISDSKNTR

KAREMLLKLA EETNIFPTSW ELSERYLFVV DRLIALDAAE

EFFKLARRTY PKKPGVPCLA DGQKELHYLP FPSP-$^C$.

(d) MREG DSΔ10: SEQ ID NO: 60:
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKP

GVPCLA DGQK-$^C$, (e) MREG DSΔ20: SEQ ID NO: 61:
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKP-$^C$,
or (f) MREG DSΔ30: SEQ ID NO: 62:
$^N$-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFK-$^C$.

2. The rAAV according to claim 1, wherein the 5' and 3' ITR sequences are self-complementary ITRs.

3. The rAAV according to claim 1, wherein the ITRs are from a different AAV source than the AAV capsid.

4. The rAAV according to claim 1, wherein the AAV capsid is selected from AAV1, AAV5, or AAV8.

5. A composition for delivery to the eye comprising the rAAV according to claim 1 and a pharmaceutically acceptable vehicle, excipient or carrier.

6. The composition according to claim 5, wherein the composition comprises about $1.5 \times 10^9$ genome copies/mL to about $1.5 \times 10^{12}$ genome copies/mL.

7. A composition comprising at least one engineered MREG protein and a pharmaceutically acceptable carrier and/or excipient, wherein the engineered MREG is:

(a) MREG USΔ10: SEQ ID NO: 57:
N-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

-continued
ADSLLSVTKL STISDSKNTR KAREMLLKLA EETNIFPTSW

ELSERYLFVV DRLIALDAAE EFFKLARRTY PKKPGVPCLA

DGQK ELHYLP FPSP-C, (b) MREG USΔ20: SEQ ID NO: 58:
N-ERALPEKEPL VSDNNPYSSF GATLVRDDEK

NLWSMPHDVS HTEADDDRTL YNLIVIRNQQ AKDSEEWQKL

NYDIHTLRQV RREVRNRWKC ILEDLGFQKE ADSLLSVTKL

STISDSKNTR KAREMLLKLA EETNIFPTSW ELSERYLFVV

DRLIALDAAE EFFKLARRTY PKKPGVPCLA DGQKELHYLP

FPSP-C, (c) MREG USΔ30: SEQ ID NO: 59:
N-VSDNNPYSSF GATLVRDDEK NLWSMPHDVS

HTEADDDRTL YNLIVIRNQQ AKDSEEWQKL NYDIHTLRQV

RREVRNRWKC ILEDLGFQKE ADSLLSVTKL STISDSKNTR

KAREMLLKLA EETNIFPTSW ELSERYLFVV DRLIALDAAE

EFFKLARRTY PKKPGVPCLA DGQKELHYLP FPSP-C.

(d) MREG DSΔ10: SEQ ID NO: 60:
N-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKP

GVPCLA DGQK-C, (e) MREG DSΔ20: SEQ ID NO: 61:
N-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFKLARRTY PKKP-C,
and (f) MREG DSΔ30: SEQ ID NO: 62:
N-CCCCGCECLE ERALPEKEPL VSDNNPYSSF

GATLVRDDEK NLWSMPHDVS HTEADDDRTL YNLIVIRNQQ

AKDSEEWQKL NYDIHTLRQV RREVRNRWKC ILEDLGFQKE

ADSLLSVTKL STISDSKNTR KAREMLLKLA EETNIFPTSW

ELSERYLFVV DRLIALDAAE EFFK-C.

\* \* \* \* \*